(12) United States Patent
Kanak et al.

(10) Patent No.: US 10,758,551 B2
(45) Date of Patent: Sep. 1, 2020

(54) METHODS AND COMPOSITIONS FOR TREATING PANCREATITIS

(71) Applicant: BAYLOR RESEARCH INSTITUTE, Dallas, TX (US)

(72) Inventors: Mazhar Adnan Kanak, Dallas, TX (US); Bashoo Naziruddin, Dallas, TX (US); Marlon F. Levy, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 15/563,304

(22) PCT Filed: Mar. 30, 2016

(86) PCT No.: PCT/US2016/024838
§ 371 (c)(1),
(2) Date: Sep. 29, 2017

(87) PCT Pub. No.: WO2016/160880
PCT Pub. Date: Oct. 6, 2016

(65) Prior Publication Data
US 2018/0117067 A1    May 3, 2018

Related U.S. Application Data

(60) Provisional application No. 62/140,735, filed on Mar. 31, 2015.

(51) Int. Cl.
*A61K 31/585* (2006.01)
*A61P 1/18* (2006.01)

(52) U.S. Cl.
CPC .............. *A61K 31/585* (2013.01); *A61P 1/18* (2018.01)

(58) Field of Classification Search
CPC .................................. A61K 31/585; A61P 1/18
See application file for complete search history.

(56) References Cited

U.S. PATENT DOCUMENTS

2004/0037902 A1* 2/2004 Pandol .................... A61K 31/12
424/756
2011/0305719 A1* 12/2011 Naziruddin ............ A61K 31/58
424/184.1

FOREIGN PATENT DOCUMENTS

WO    WO 2010/053655        5/2010

OTHER PUBLICATIONS

Oncogene, 25, 6887-6899 (Year: 2006).*
Kaileh et al, The Journal of Biological Chemistry, vol. 282, No. 7, 4253-4264. (Year: 2007).*
SoRelle et al, Diabetologia, 56:814-824. (Year: 2013).*
Peng et al, Transplantation Proceedings, 42, 2058-2061. (Year: 2010).*
Grover et al, BMC Genomics, 11 (Suppl 4):S25. (Year: 2010).*
International Search Report and Written Opinion issued in Application No. PCT/US16/24838, dated Jun. 23, 2016.

* cited by examiner

*Primary Examiner* — Sudhakar Katakam
(74) *Attorney, Agent, or Firm* — Norton Rose Fulbright US LLP

(57) ABSTRACT

It was discovered that NF-κB signaling pathway plays a central role in pancreatitis, and inhibition of NF-κB signaling has the potential to reduce the incidence of pancreatitis and protect pancreatic tissues from inflammatory damage. Aspects of the disclosure relate to a method for inhibiting or treating pancreatitis in a subject in need thereof comprising administering a therapeutically effective amount of an NF-κB signaling pathway inhibitor to the subject.

9 Claims, 27 Drawing Sheets

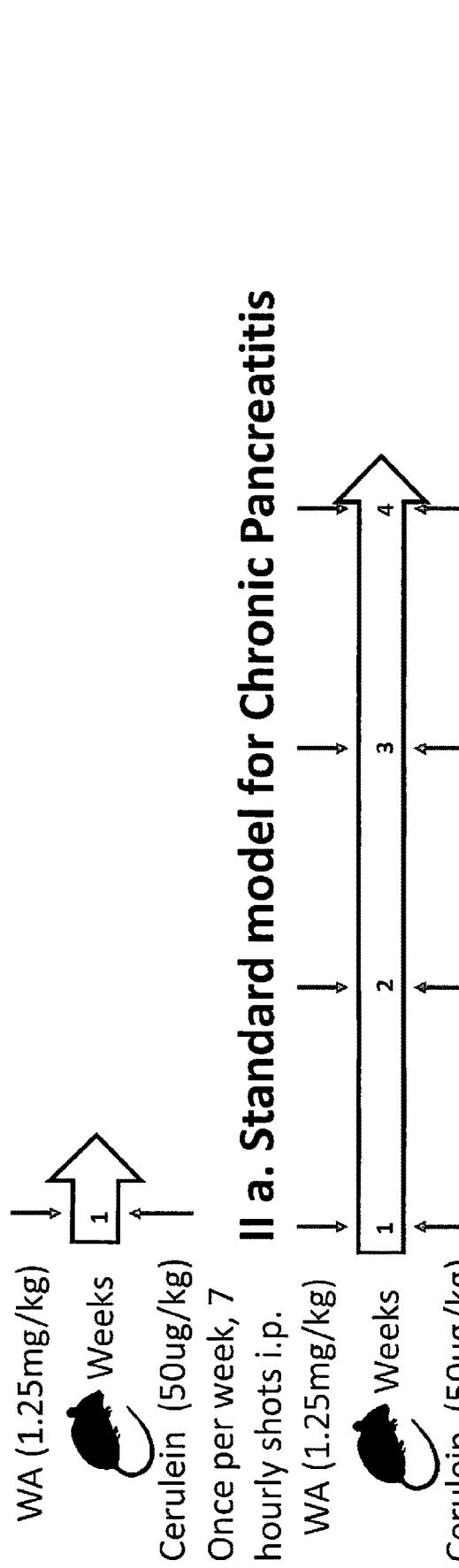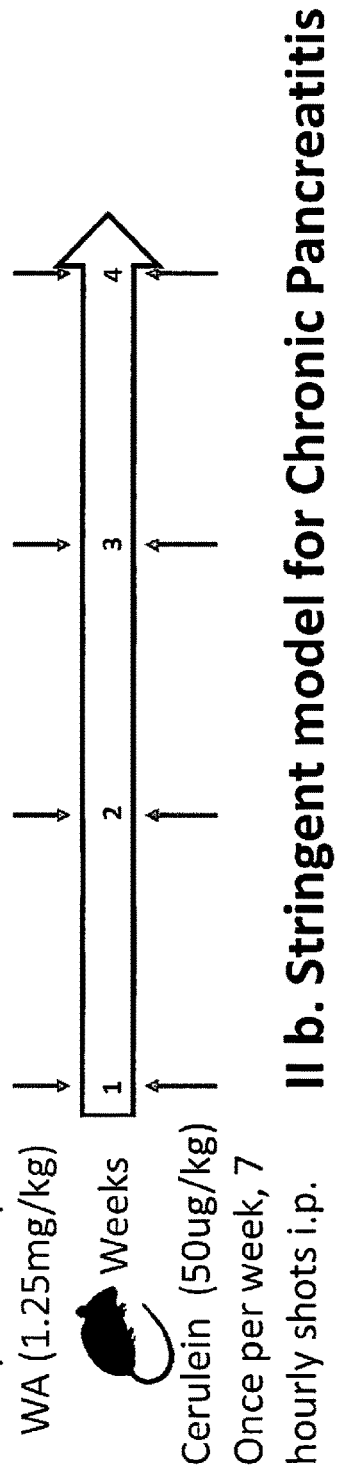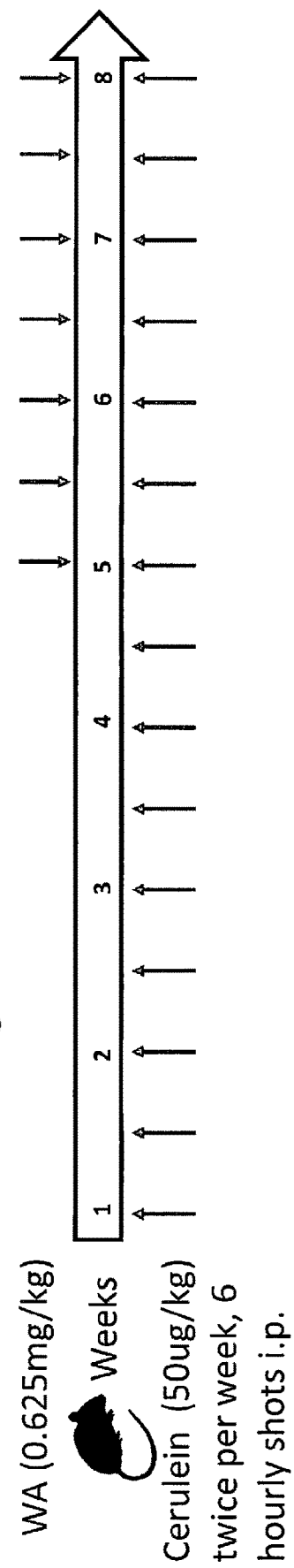
FIG. 1

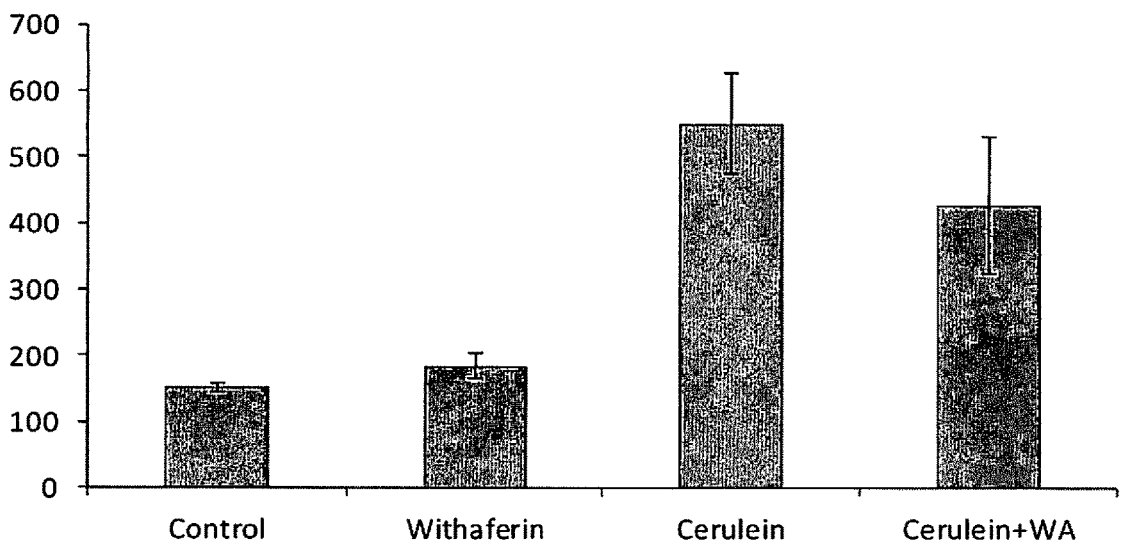
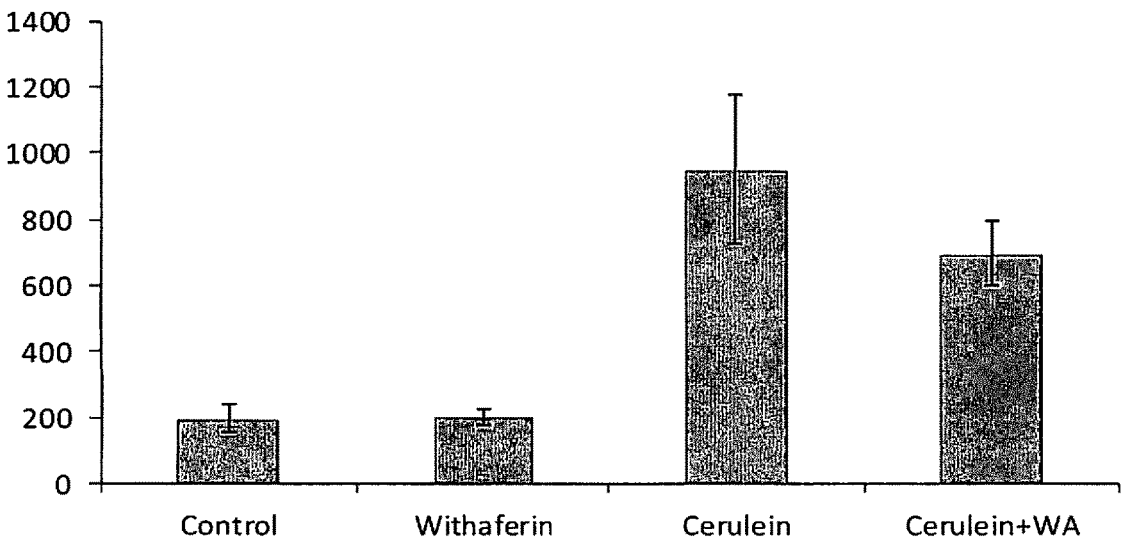
FIG. 4

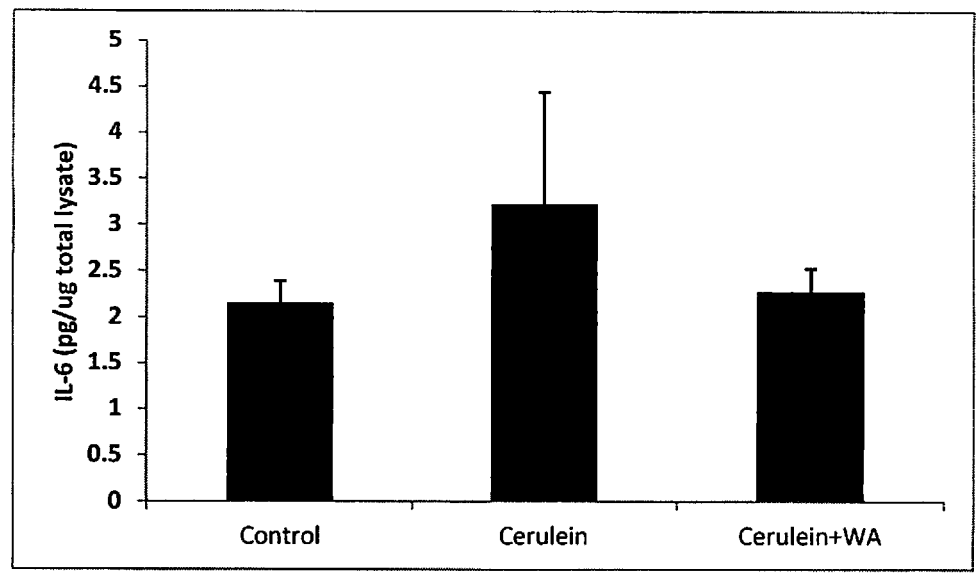
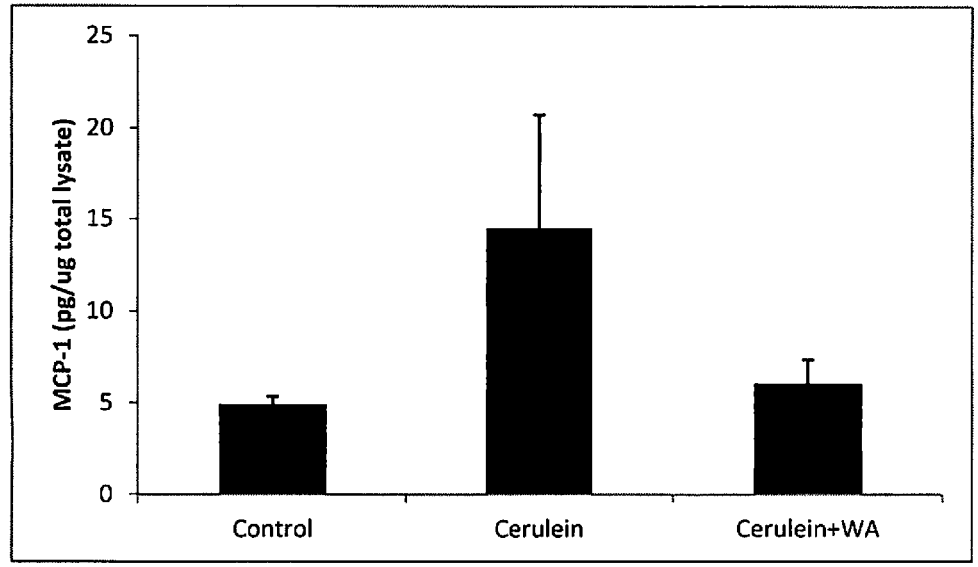
FIG. 5A-B

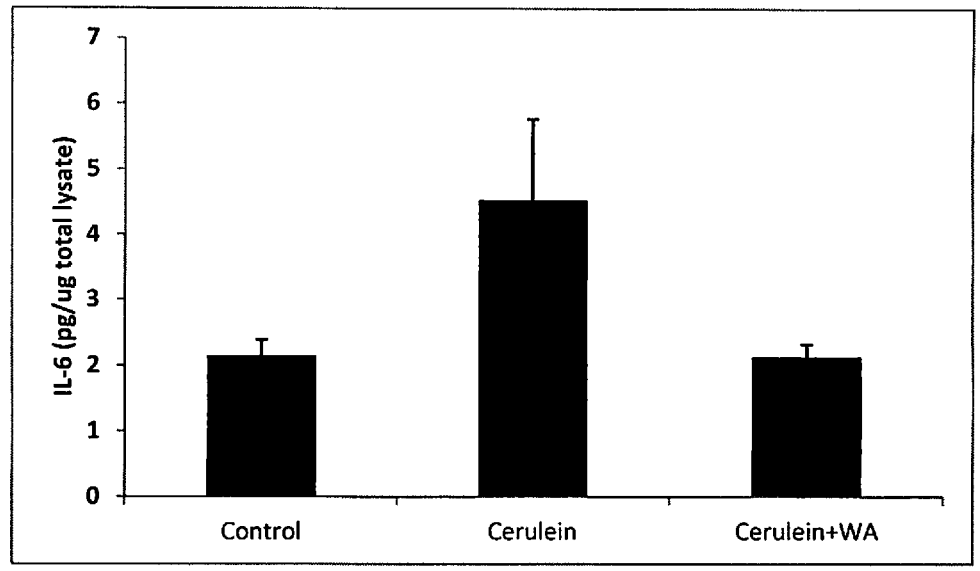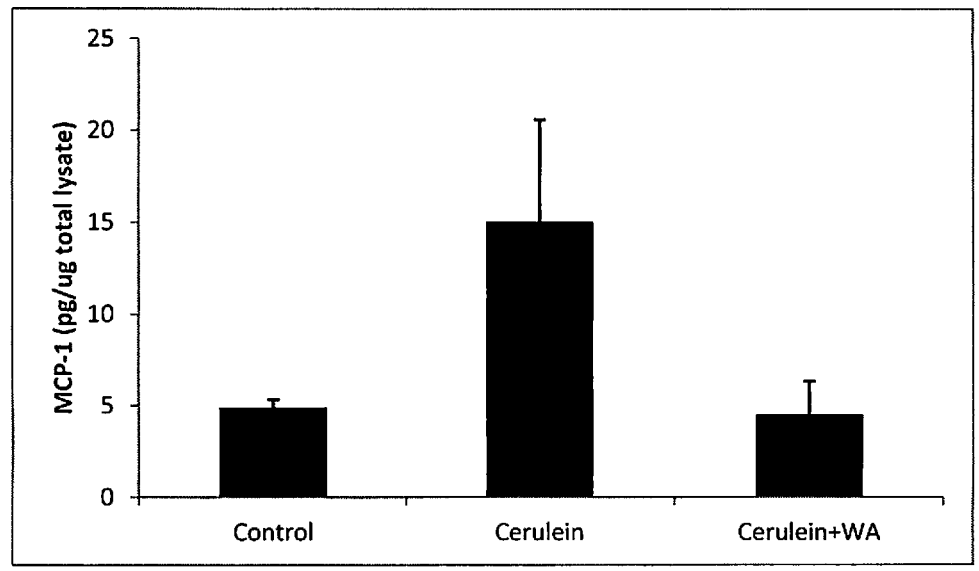
FIG. 6A-B

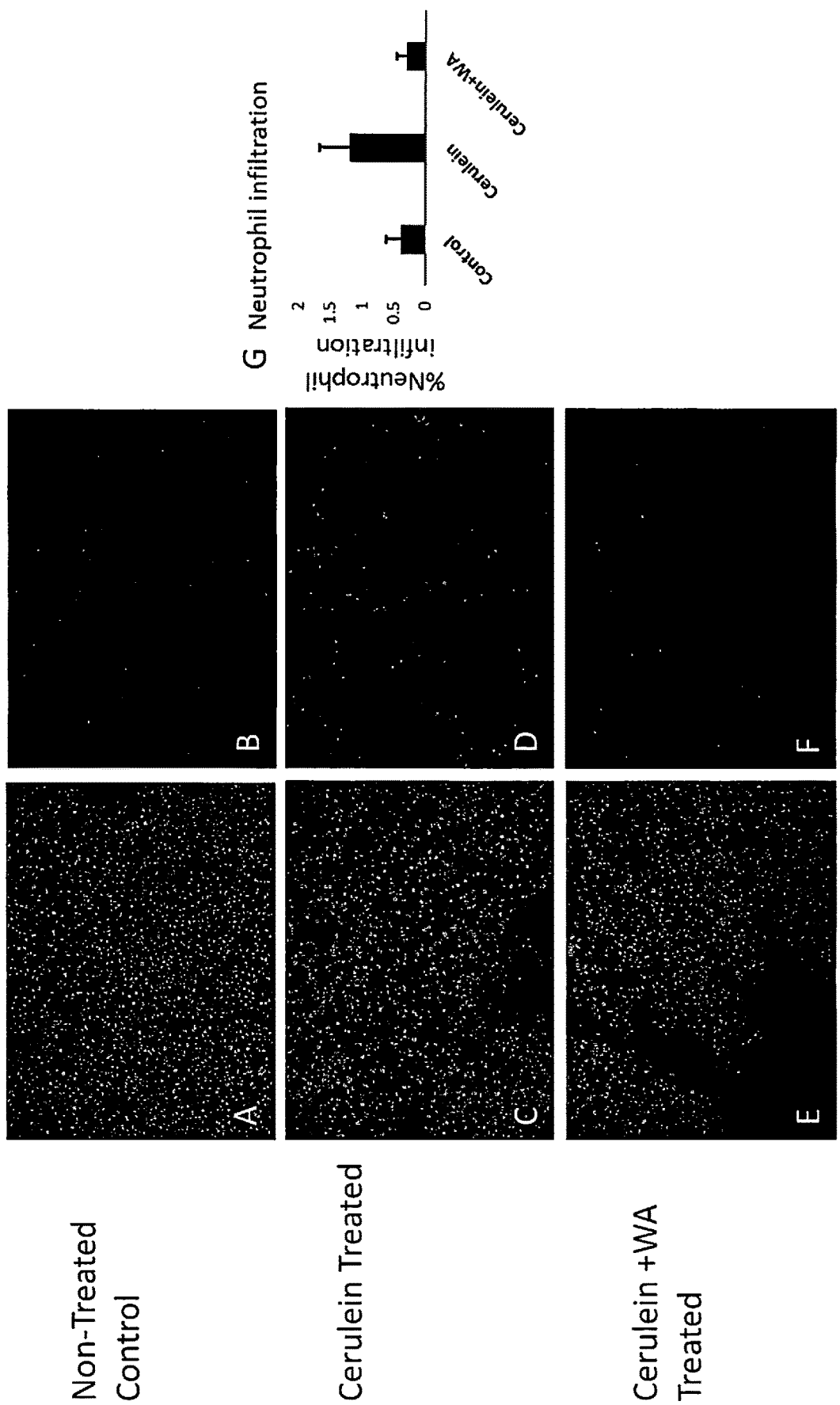
FIG. 7A-G

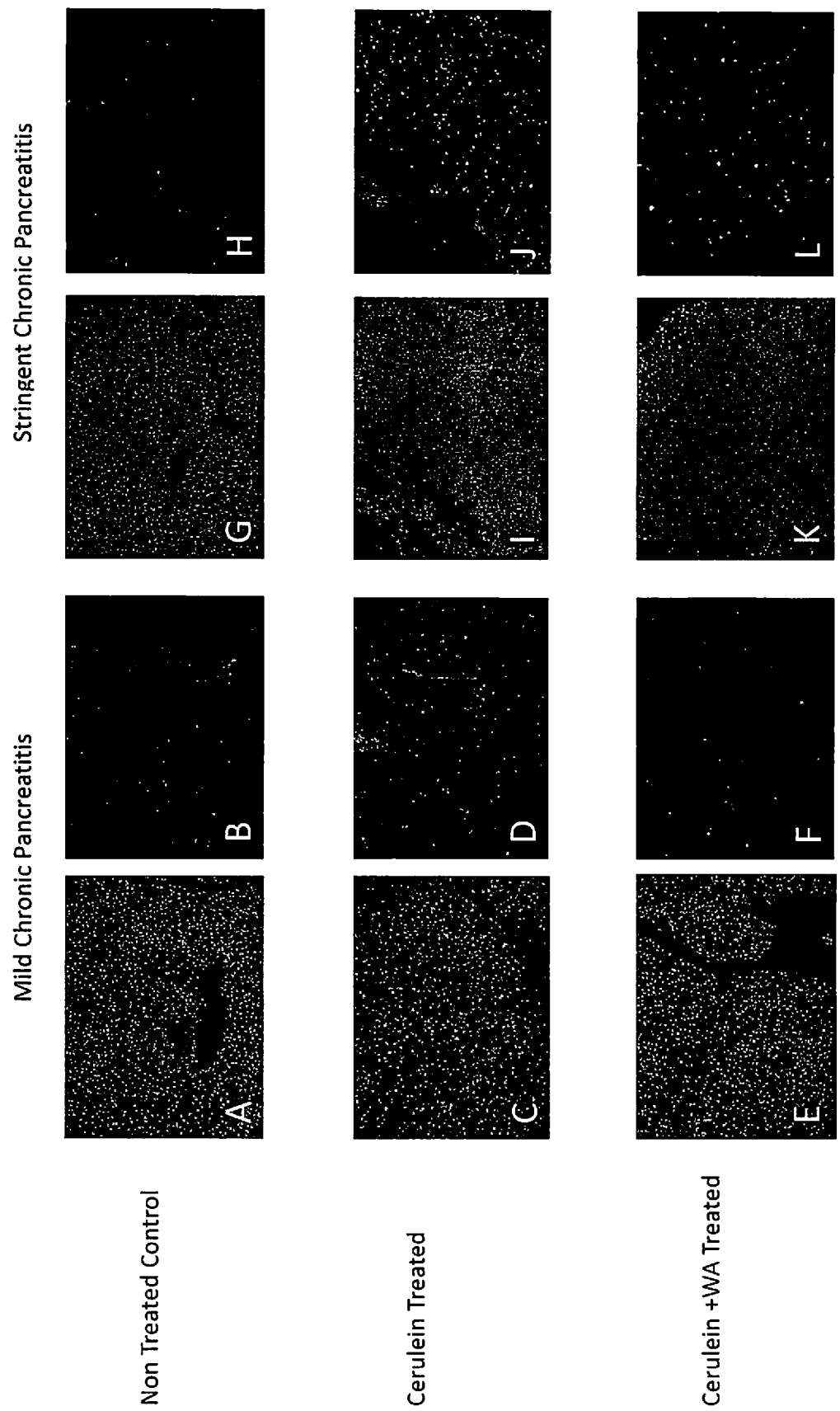
FIG. 8A-L

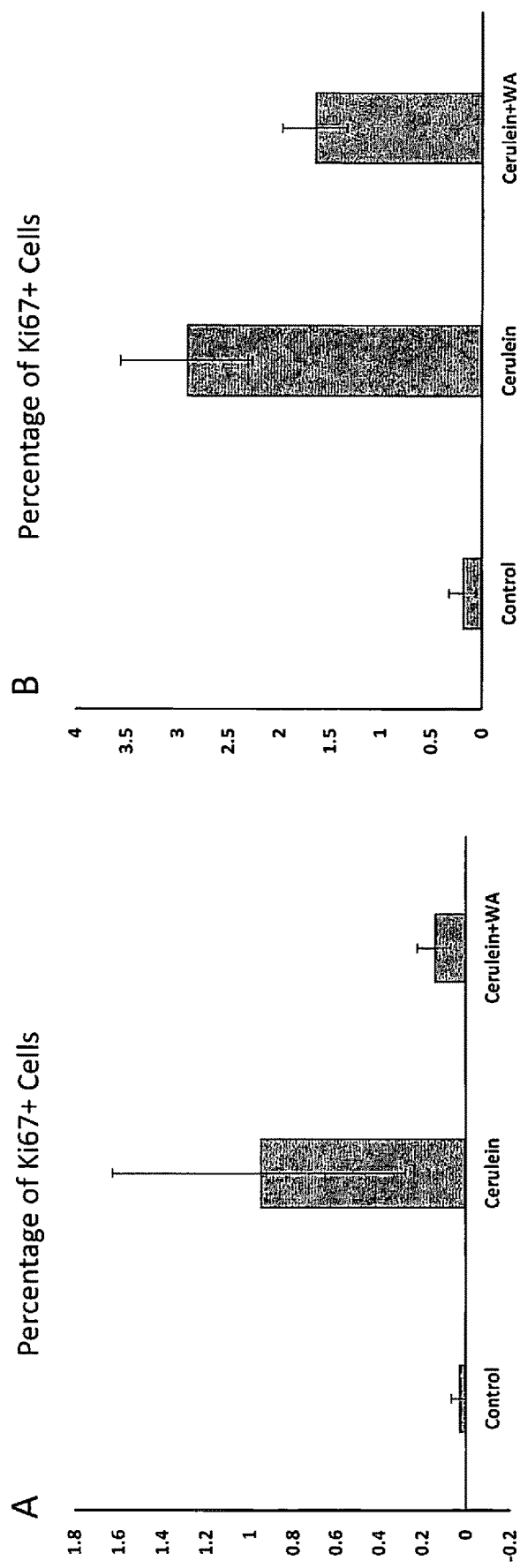
FIG. 9A-B

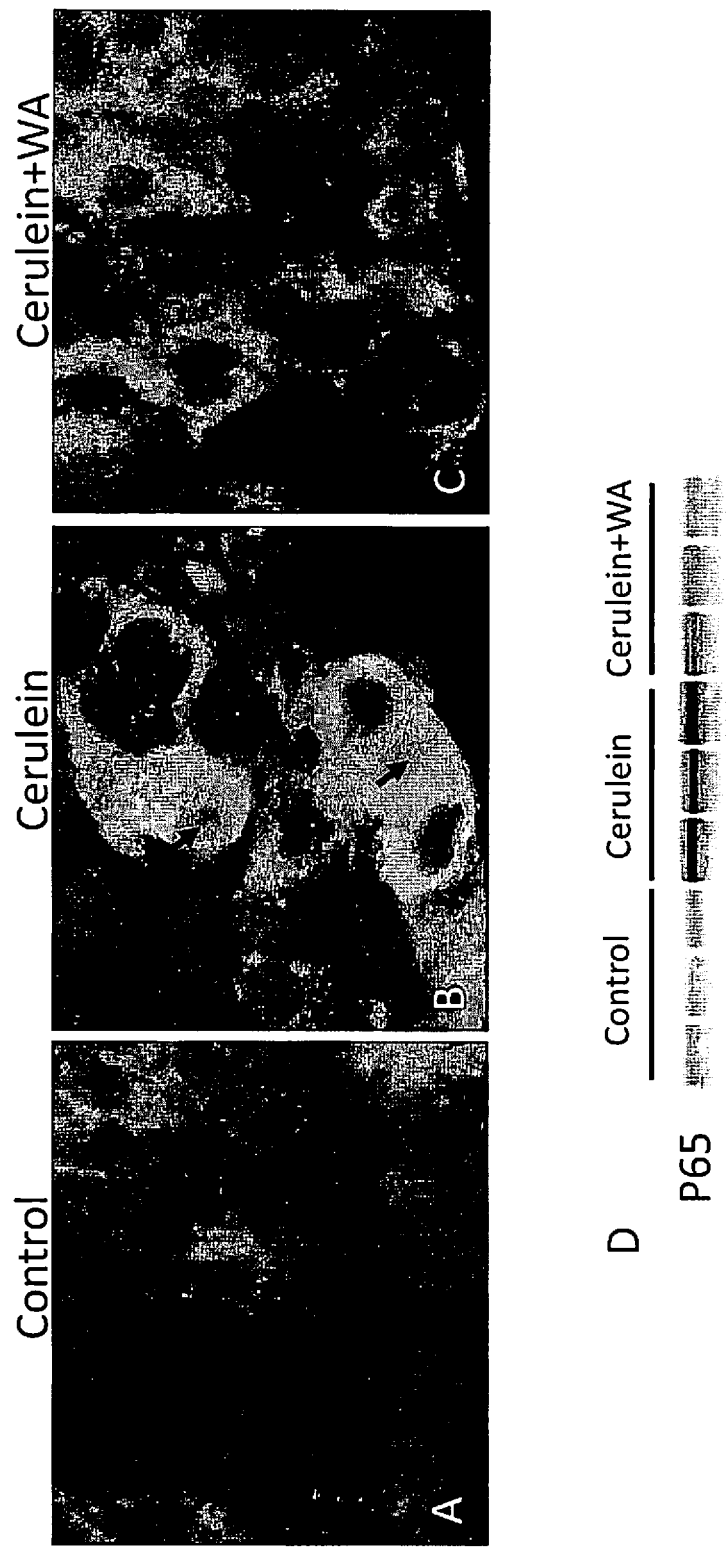
FIG. 10A-D

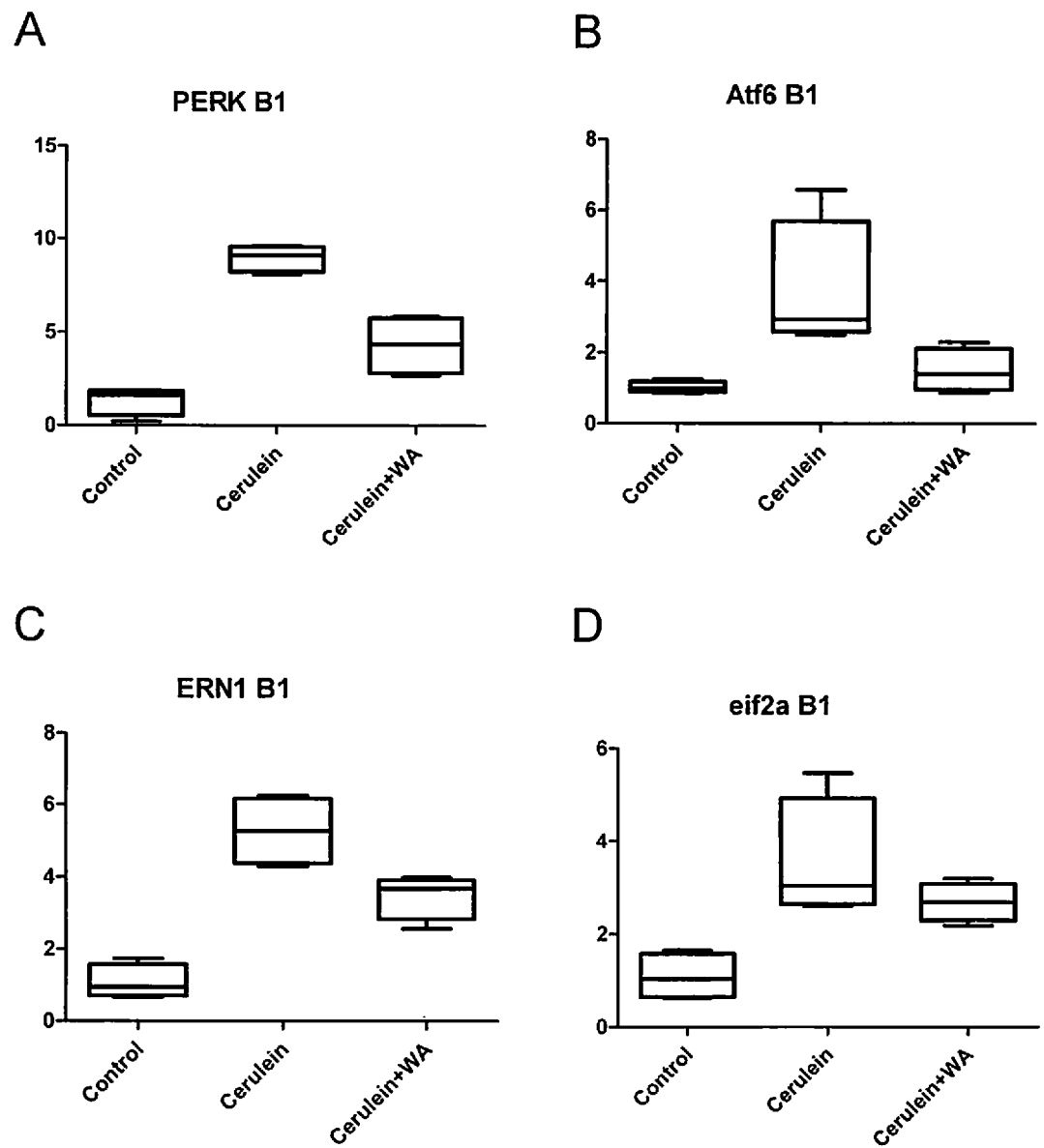
FIG. 11A-D

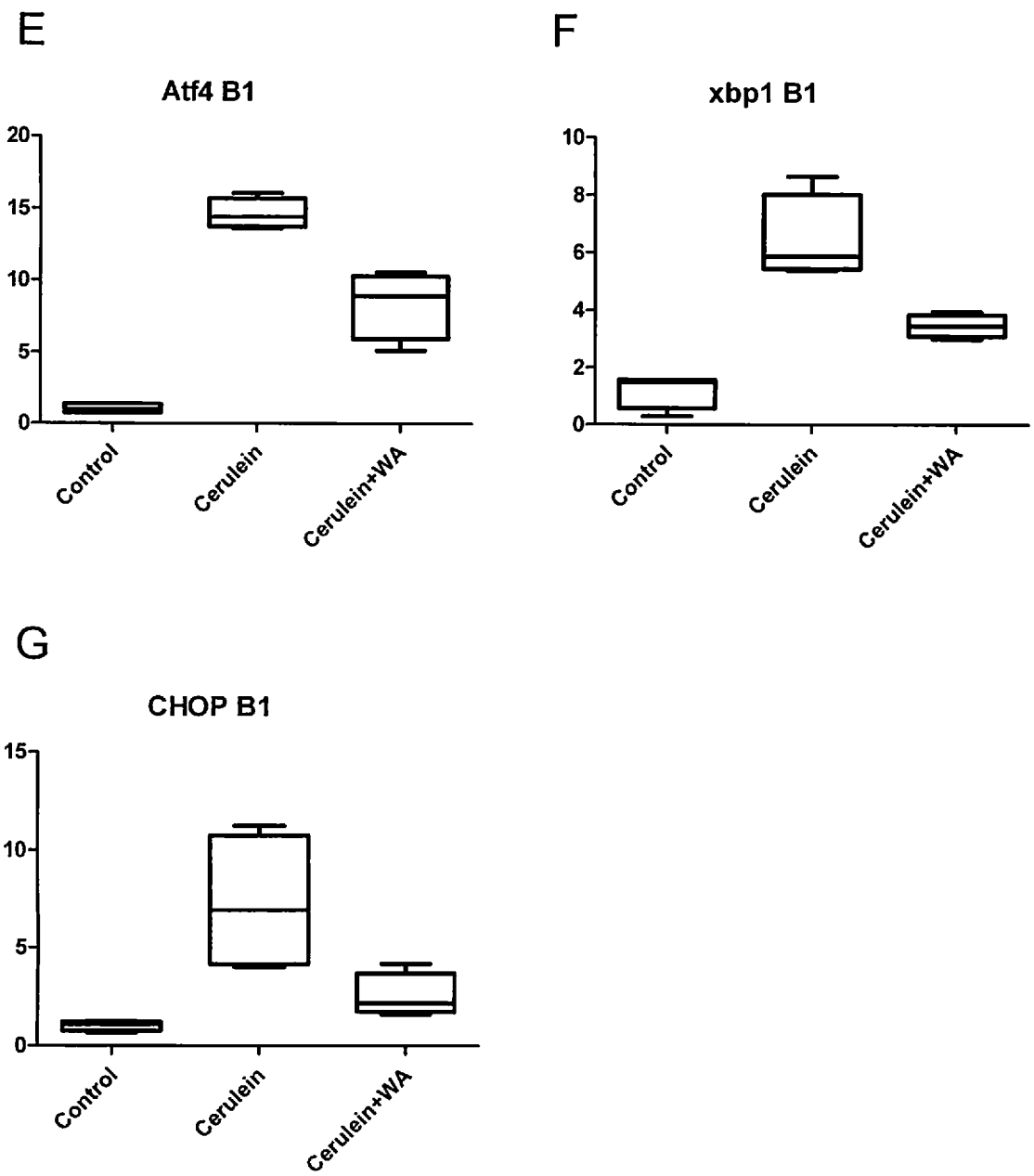
FIG. 11E-G

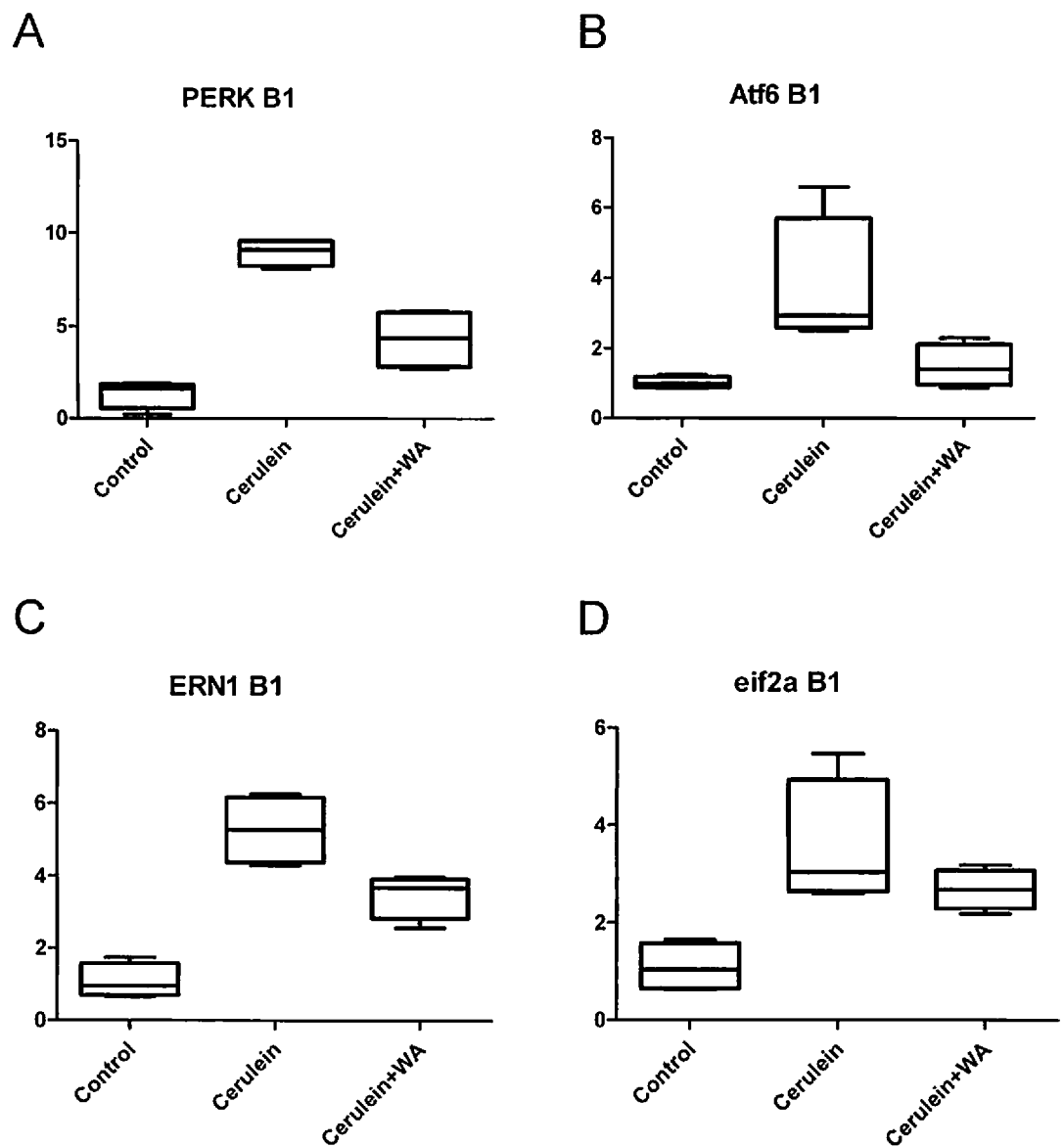
FIG. 12A-D

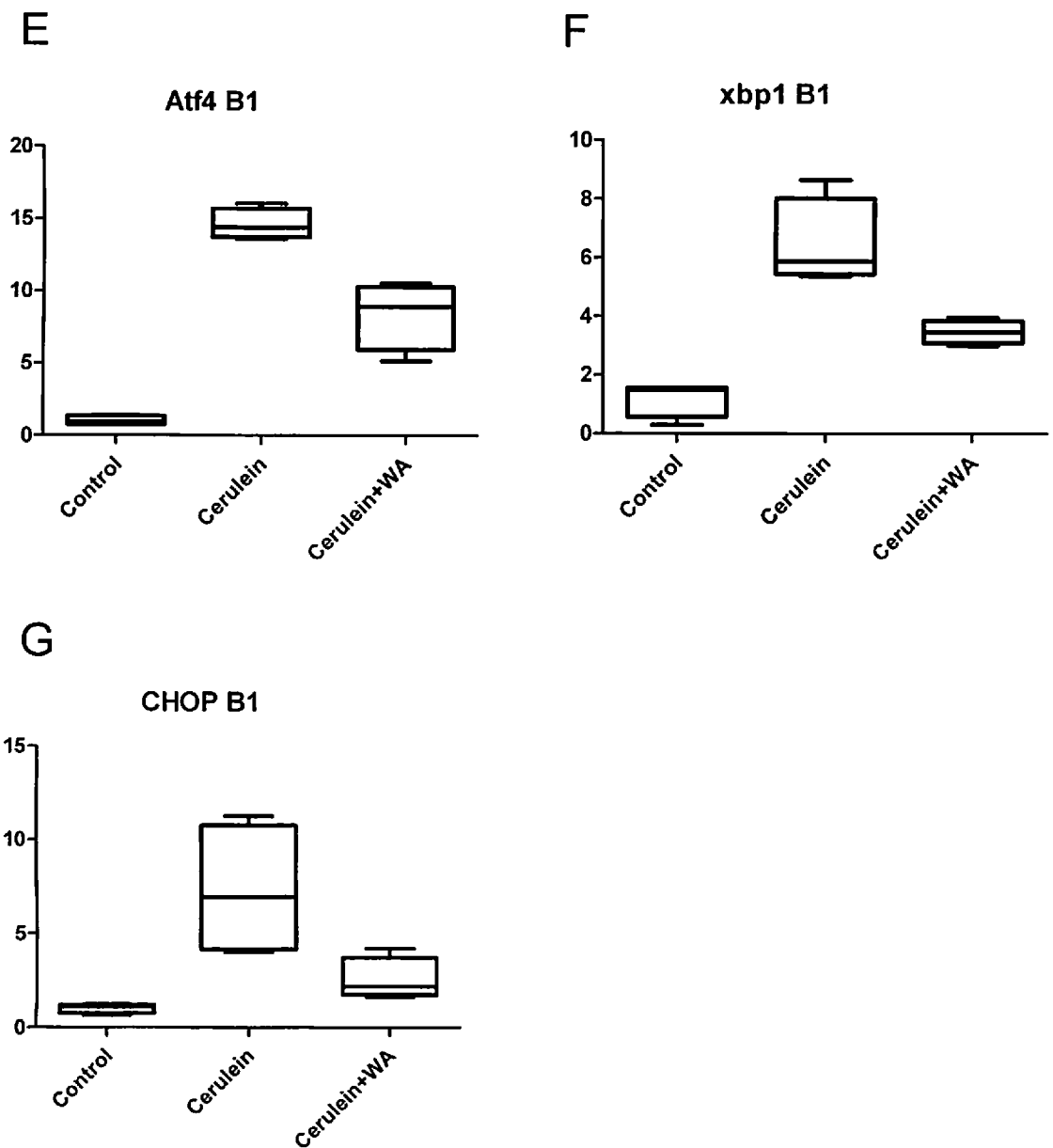
FIG. 12E-G

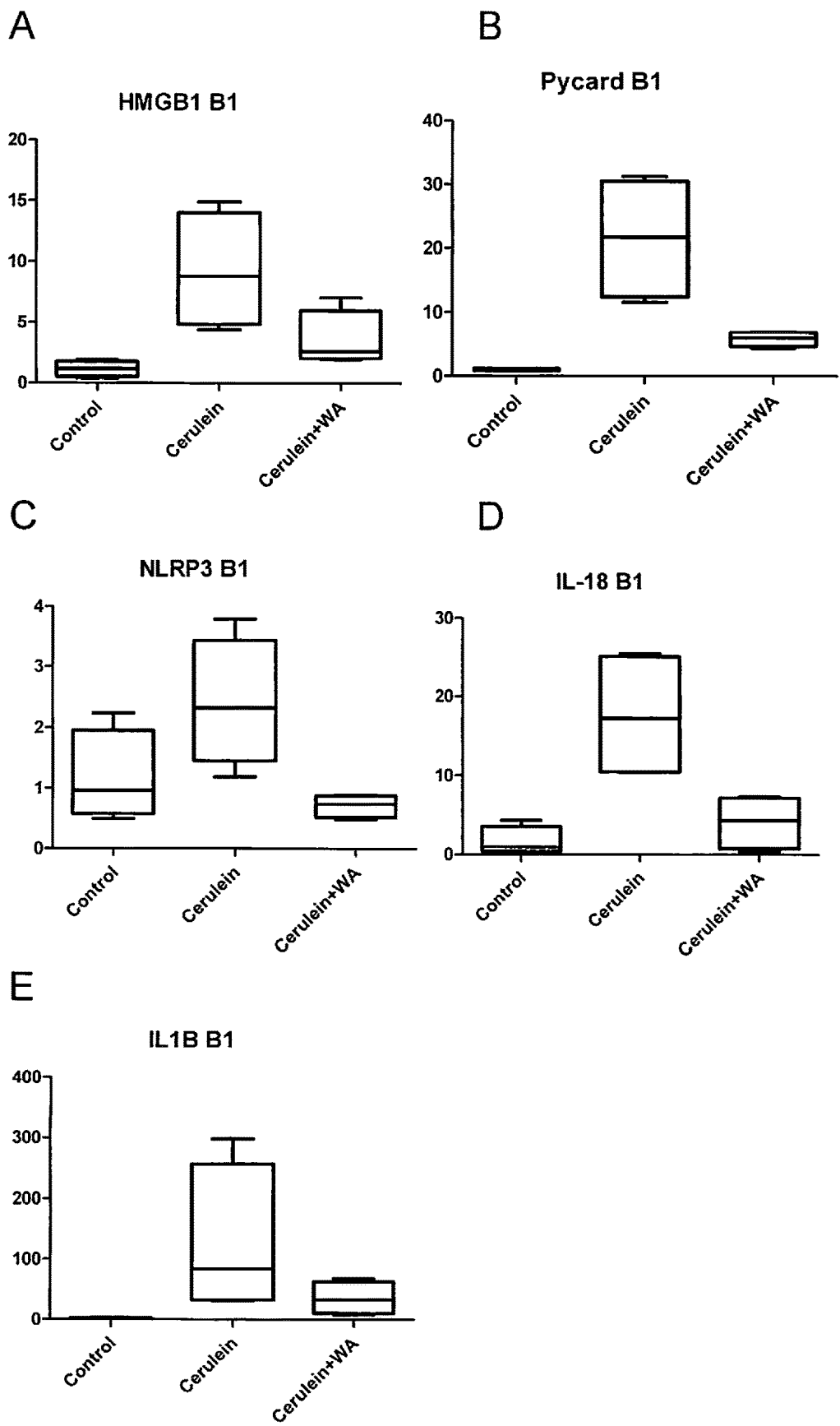
FIG. 13A-E

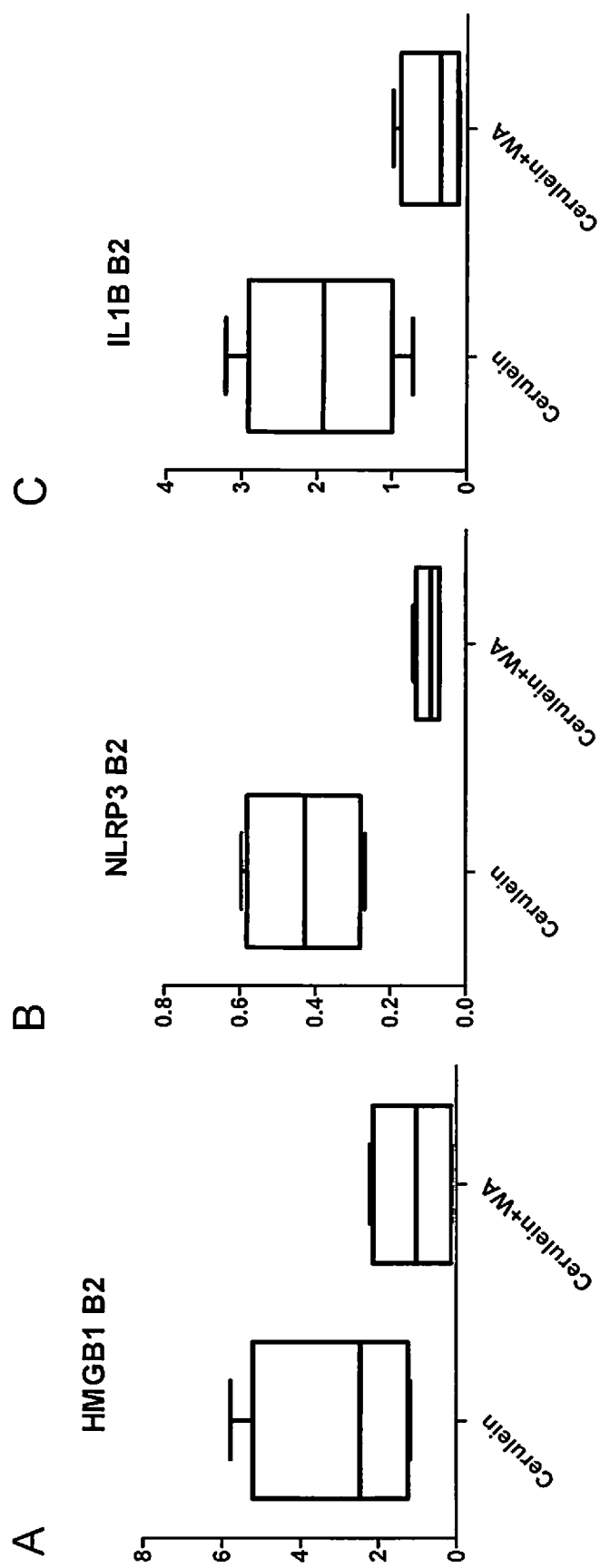
FIG. 14A-C

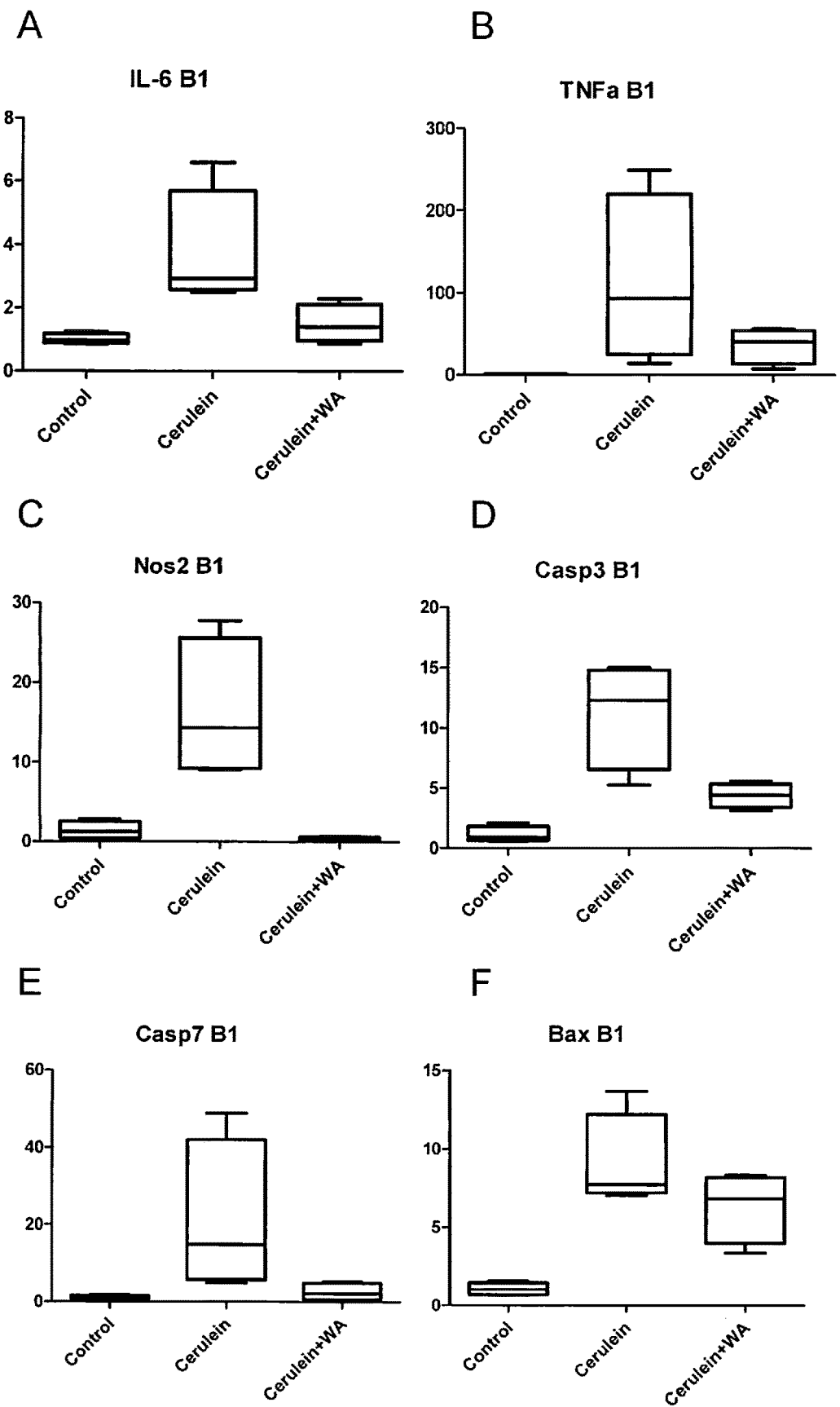
FIG. 15A-F

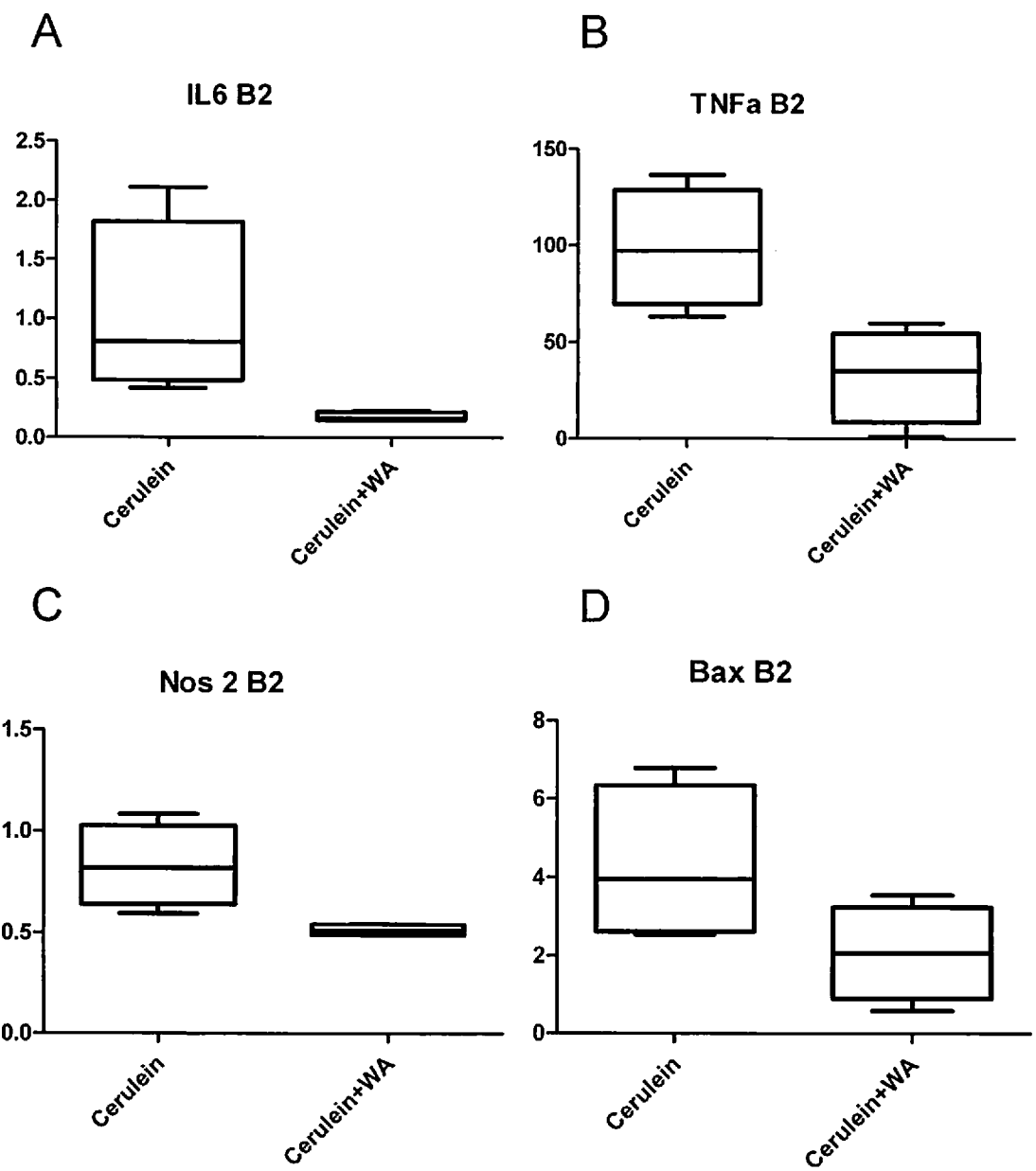
FIG. 16A-D

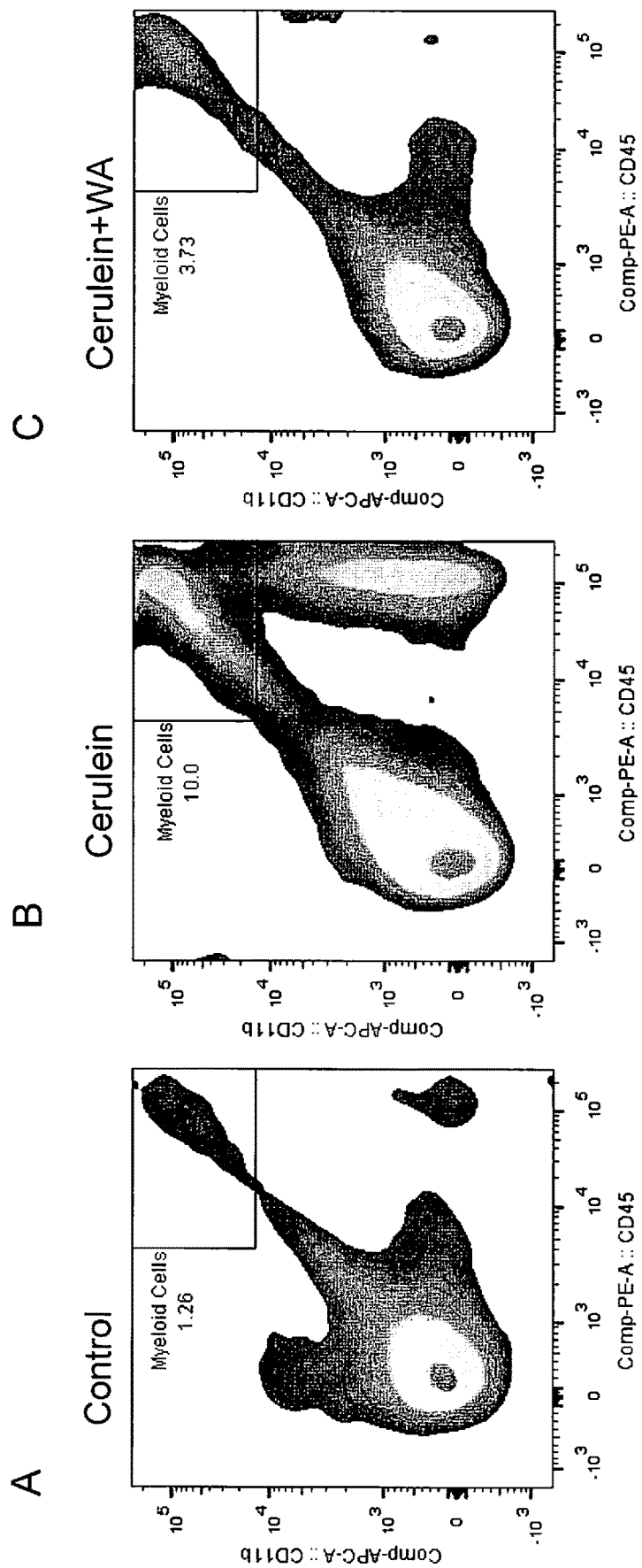
FIG. 18A-C

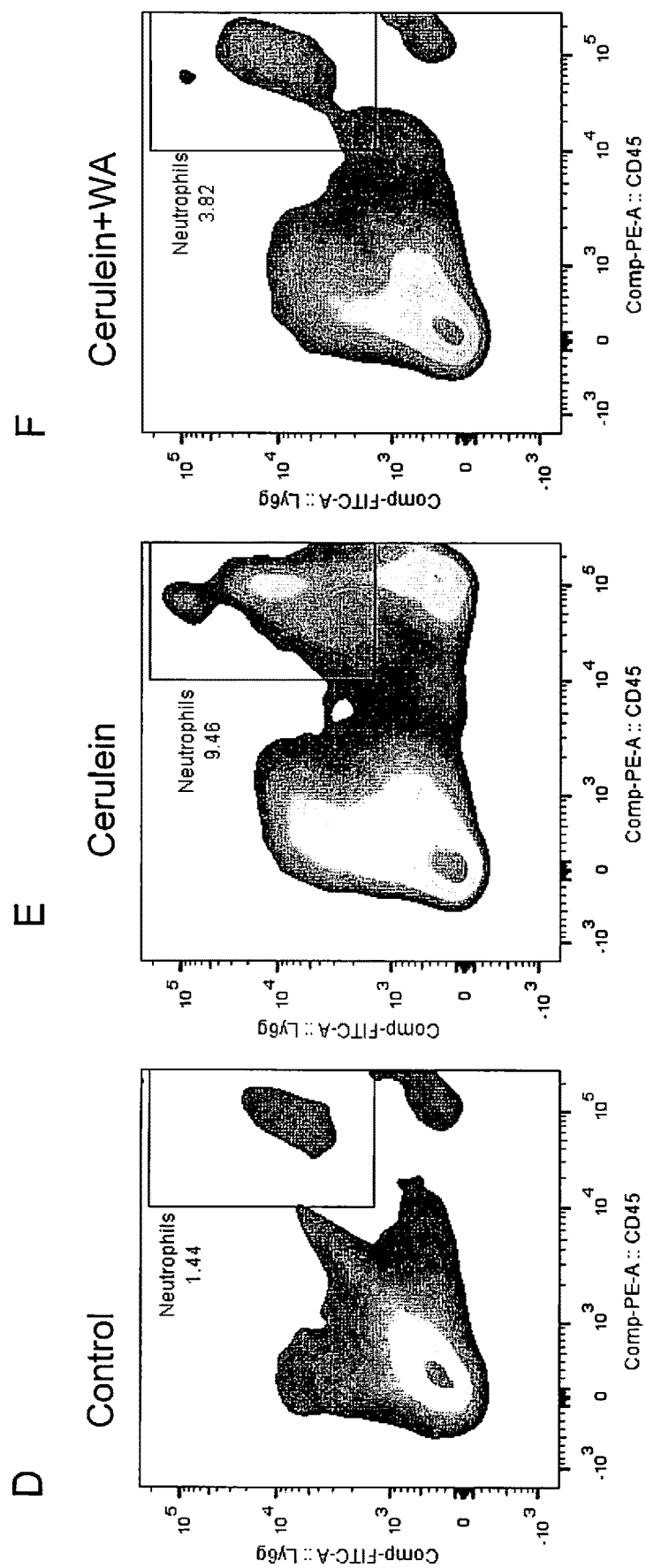
FIG. 18D-F

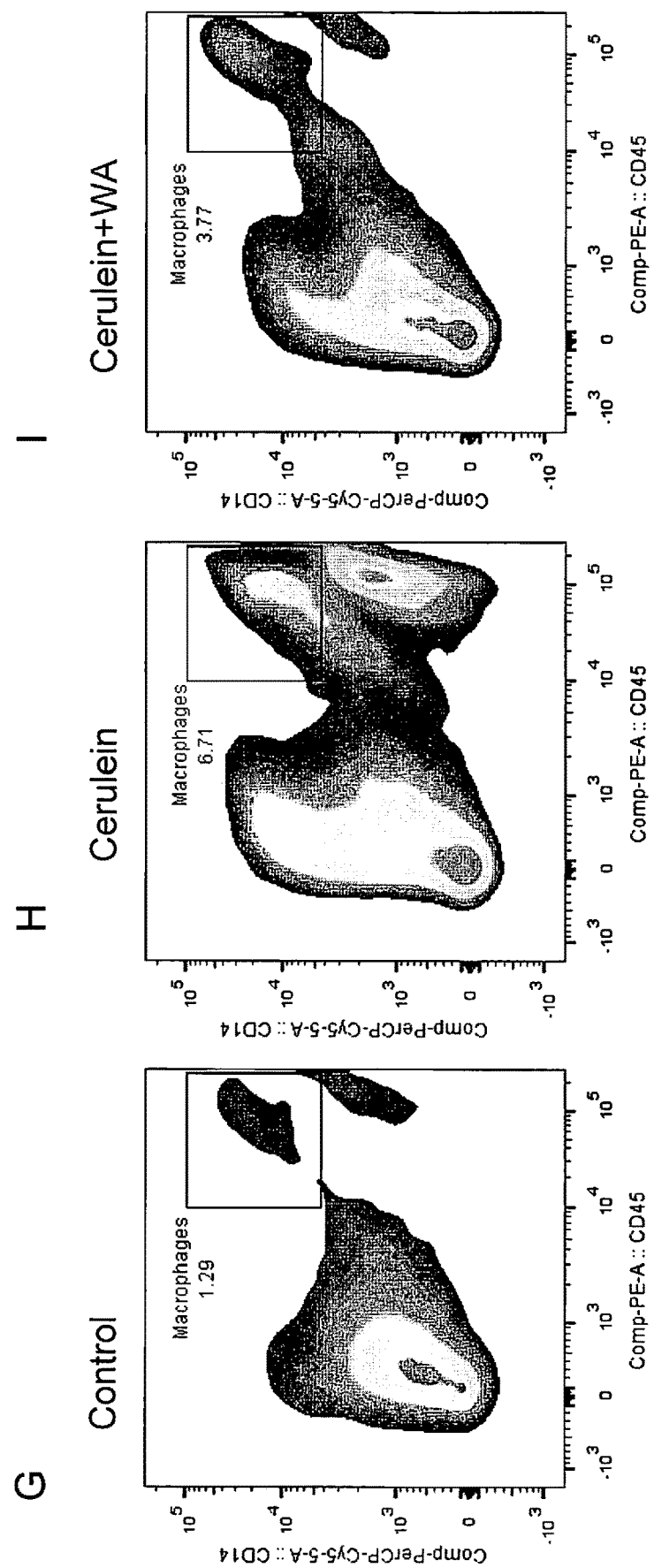
FIG. 18G-I

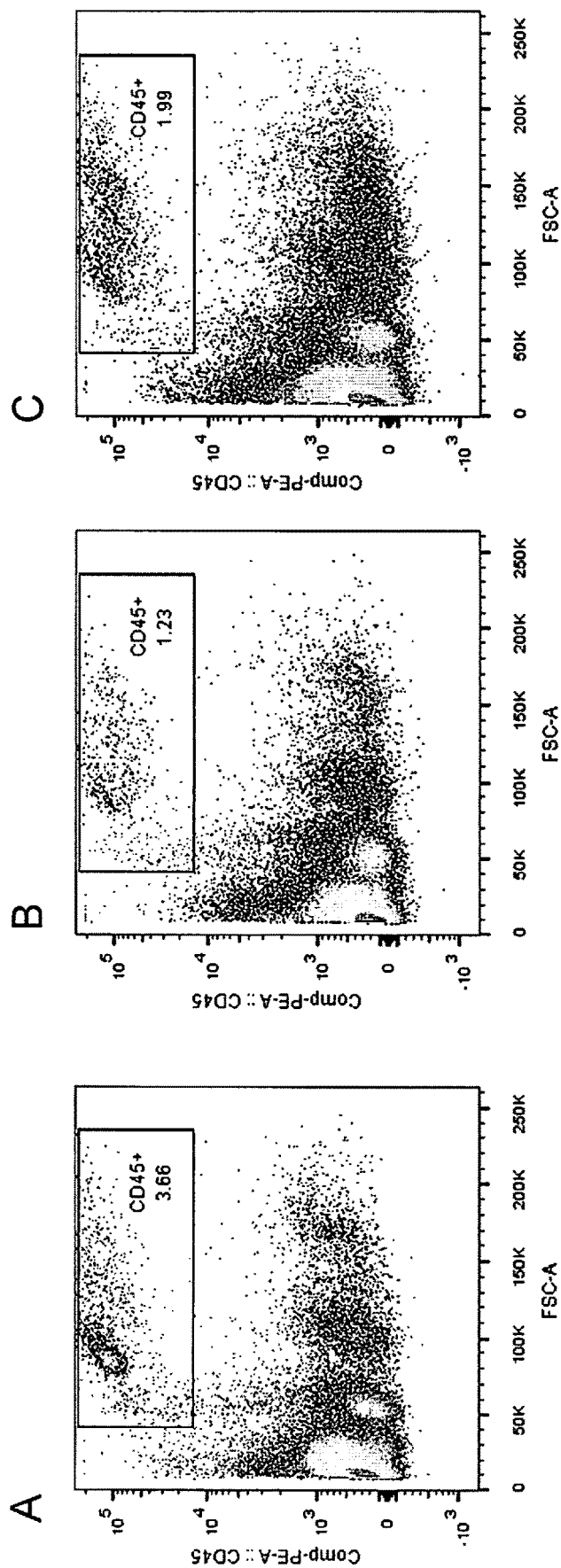
FIG. 19A-C

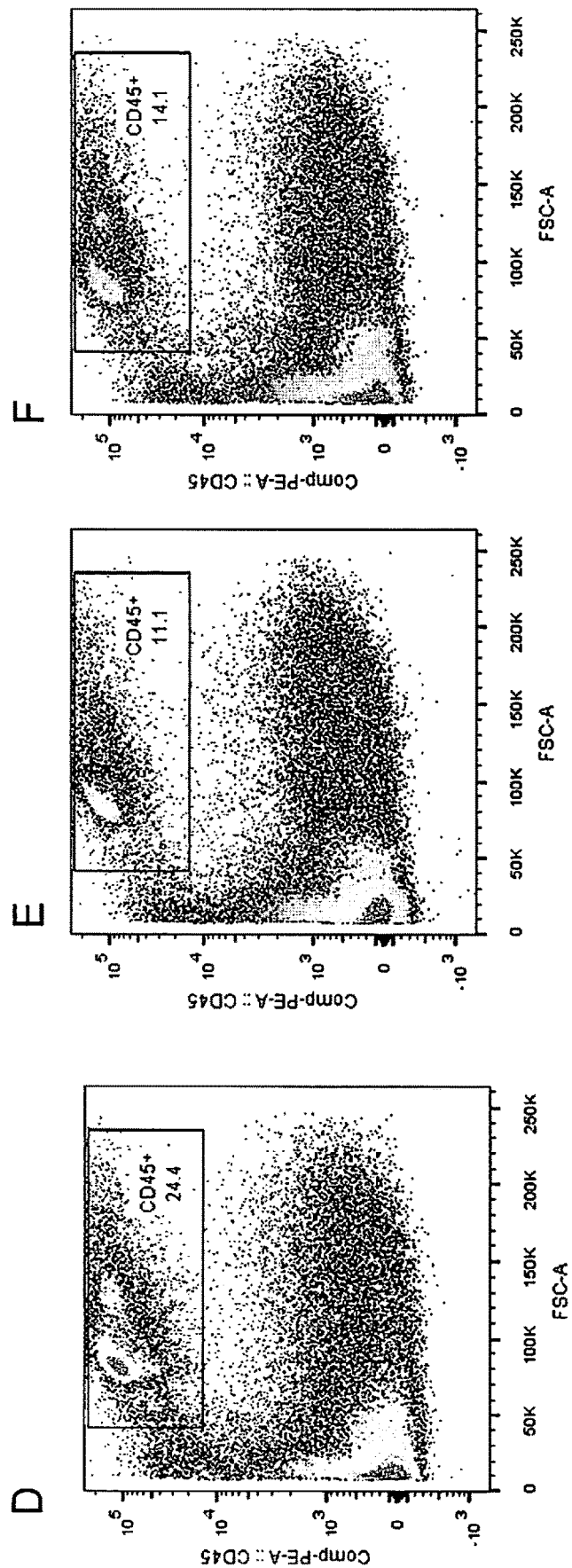
FIG. 19D-F

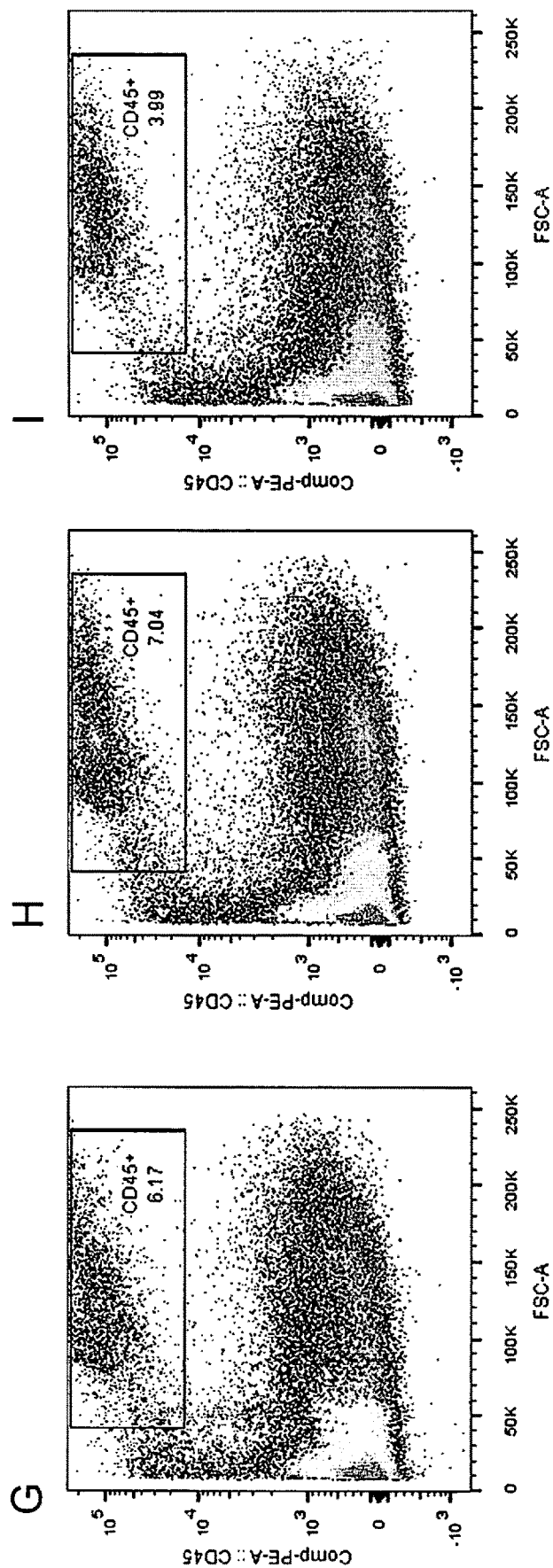
FIG. 19G-I

METHODS AND COMPOSITIONS FOR TREATING PANCREATITIS

CROSS-REFERENCE TO RELATED APPLICATIONS

This application is a national phase under 35 U.S.C. § 371 of International Application No. PCT/US2016/024838, filed Mar. 30, 2016, which claims the benefit of priority to U.S. Provisional Patent Application No. 62/140,735, filed Mar. 31, 2015, the entire contents of each of which are hereby incorporated by reference in their entirety.

BACKGROUND OF THE INVENTION

I. Field of the Invention

Embodiments are directed generally to biology and medicine. In certain aspects there are methods and compositions for treating pancreatitis.

II. Background

Pancreatitis is defined as inflammation of the pancreas. There are two main types, acute pancreatitis and chronic pancreatitis. Symptoms of pancreatitis include pain in the upper abdomen, nausea and vomiting. The pain often goes into the back and is usually severe. In acute pancreatitis a fever may occur and symptoms typically resolve in a few days. In chronic pancreatitis weight loss, fatty stool, and diarrhea may occur. Complications may include infection, bleeding, diabetes, or problems with other organs.

The most common causes of acute pancreatitis are gallstones and heavy alcohol use. Other causes include direct trauma, certain medications, infections such as mumps, and tumors among others. Chronic pancreatitis may develop as a result of acute pancreatitis. It is most commonly due to many years of heavy alcohol use. Other causes include high levels of blood fats, high blood calcium, some medications, and certain genetic disorders such as cystic fibrosis among others.

People with acute pancreatitis are treated with IV fluids and pain medications in the hospital. In up to 25% of patients, the pancreatitis can be severe and patients may need to be admitted to an intensive care unit (ICU). In the ICU, the patient is closely watched because pancreatitis can damage the heart, lungs, or kidneys. Some cases of severe pancreatitis can result in death of pancreatic tissue. In these cases, surgery may be necessary to remove the dead or damaged tissue if an infection develops. An acute attack of pancreatitis usually lasts a few days.

Chronic pancreatitis can be difficult to treat. Doctors may try to relieve the patient's pain and improve the nutrition problems. In some instances, pancreatic enzymes, insulin, or a low-fat diet may help the chronic pancreatitis. Surgery may help relieve abdominal pain, restore drainage of pancreatic enzymes or hormones, treat chronic pancreatitis caused by blockage of the pancreatic duct, or reduce the frequency of attacks. Eventhough other inflammatory diseases are often treated with anti-inflammatory medications and/or immunosuppressants, there are no standard therapeutic strategies for pharmacologically reducing inflammation in pancreatitis or for treating the disease in any way other than pain management. Furthermore, pancreatitis has been shown to have a higher risk to develop into pancreatic cancer. There is a need in the art for treatments of pancreatitis that reduce inflammation, provide cellular protection, and block or inhibit the progression of the disease, either from acute to chronic pancreatitis or from chronic pancreatitis into more complicated pathologies, such as pancreatic cancer.

SUMMARY OF THE INVENTION

The current disclosure fulfills the aforementioned need in the art by providing therapeutics that treat pancreatitis and/or inhibit the progression of pancreatitis. It was discovered that NF-κB signaling pathway plays a central role in pancreatitis, and inhibition of NF-κB signaling has the potential to reduce the incidence of pancreatitis and protect pancreatic tissues from inflammatory damage. Aspects of the disclosure relate to a method for inhibiting or treating pancreatitis in a subject in need thereof comprising administering a therapeutically effective amount of an NF-κB signaling pathway inhibitor to the subject. The NF-κB signaling pathway and components thereof are known in the art and also depicted in FIG. 20. Accordingly, the NF-κB signaling pathway inhibitor may be a modulator of a protein of the pathway that inhibits active NF-κB signaling.

Additional aspects of the disclosure relate to methods for alleviating one or more symptoms associated with acute pancreatitis and/or chronic pancreatitis in a subject in need thereof comprising administering a therapeutically effective amount of an NF-κB signaling pathway inhibitor to the subject. In certain embodiments, the symptoms may include or exclude one or more of pain, such as abdominal pain, abdominal pain that radiates into the back, and abdomen tenderness, nausea, vomiting, fever, increased heart rate, and weight loss.

A further aspect of the disclosure relates to a method for for reducing pancreatic inflammation in a subject in need thereof comprising administering a therapeutically effective amount of an NF-κB signaling pathway inhibitor to the subject.

Further aspects relate to a method for inhibiting pancreatic acinar cell atrophy in a subject in need thereof, the method comprising administering a therapeutically effective amount of an NF-κB signaling pathway inhibitor to the subject.

In some embodiments, the subject has been diagnosed with acute or chronic pancreatitis. In some embodiments, the subject has been diagnosed with chronic pancreatitis. In some embodiments, the subject is not one that has been diagnosed with pancreatic cancer or is not at risk of getting pancreatic cancer. In some embodiments, the patient is not receiving cancer therapy or pancreatic cancer therapy. In some embodiments, the method is for treating chronic or acute pancreatitis by inhibiting the progression of pancreatitis in the subject. In some embodiments, the patient has been determined not to have pancreatic cancer. In some embodiments, the patient exhibits symptoms of pancreatitis and/or does not exhibit symptoms of pancreatic cancer.

In some embodiments, the method is for inhibiting the progression of pancreatitis, such as the progression from acute to chronic pancreatitis or the progression of chronic pancreatitis into other disorders, such as pancreatic cancer.

In some embodiments, the NF-κB signaling pathway inhibitor is selected from 2-Amino-6-[2-(cyclopropylmethoxy)-6-hydroxyphenyl]-4-(4-piperidinyl)-3-pyridinecarbonitrile (ACHP); 2-Amino-7-(1-methylethyl)-5-oxo-5H-[1]benzopyrano[2,3-b]pyridine-3-carboxylic acid (Amlexanox); (3E,4S)-3-[2-[(1R,4aS,5R,6R,8aS)-Decahydro-6-hydroxy-5-(hydroxymethyl)-5, 8a-dimethyl-2-methylene-1-naphthalenyl]ethylidene]dihydro-4-hydroxy-2

(3H)-furanone (Andrographolide); (3R,4R)-4-[(3,4-Dimethoxyphenyl)methyl]dihydro-3-[(4-hydroxy-3-methoxyphenyl)methyl]-2(3H)-furanone (Arctigenin); (2E)-3-[[4-(1,1-Dimethylethyl)phenyl]sulfonyl]-2-propenenitrile (Bay 11-7085); (2E)-3-[(4-Methylphenyl)sulfonyl]-2-propenenitrile (Bay 11-7821); (6E)-6,7,8,9-Tetradeoxy-N-[(3S,6S)-hexahydro-1-methyl-2-oxo-6-[(1-oxotetradecyl)oxy]-1H-azepin-3-yl]-8-methyl-2-O-methyl-D-gulo-Non-6-enonamide (Bengamide B); 3-(3,4-Dihydroxyphenyl)-2-propenoic acid 2-phenylethyl ester (CAPE); 2E)-1-(2,4-Dihydroxy-6-methoxyphenyl)-3-phenyl-2-propen-1-one (Cardamonin); (9β,13α,14β,20α)-3-Hydroxy-9,13-dimethyl-2-oxo-24,25,26-trinoroleana-1(10),3,5,7-tetraen-29-oic acid (Celastrol); 1-[3,5-Bis(1,1-dimethylethyl)-4-hydroxyphenyl]-2-[2-[(3-hydroxypropyl)amino]-5,6-dimethyl-1H-benzimidazol-1-yl]ethanone (CID 2858522); (3R,5aS,6S,10aR)-2,3,5a,6-Tetrahydro-6-hydroxy-3-(hydroxymethyl)-2-methyl-10H-3,10a-epidithiopyrazino[1,2-a]indole-1,4-dione (Gliotoxin); 5,3'-Diallyl-2,4'-dihydroxybiphenyl (Honokiol); (6aS,10aS)-3-(1,1-Dimethylheptyl)-6a,7,10,10a-tetrahydro-1-hydroxy-6,6-dimethyl-6H-dibenzo[b, d]pyran-9-methanol (Dexanabinol); (4Z)-4-(2-Amino-1,5-dihydro-5-oxo-4H-imidazol-4-ylidene)-2-bromo-4,5,6,7-tetrahydropyrrolo[2,3-c]azepin-8(1H)-one (10 Z-Hymenialdisine); N-(4-Pyrrolidin-1-yl-piperidin-1-yl)-[4-(4-benzo[b]thiophen-2-yl-pyrimidin-2-ylamino)phenyl]carboxamide hydrochloride (IKK 16); N-[3,5-Bis(trifluoromethyl)phenyl]-5-chloro-2-hydroxybenzamide (IMD 0354); 2-(3,4-Dihydroxyphenyl)-5,7-dihydroxy-4H-1-benzopyran-4-one (Luteolin); N-[(Phenylmethoxy)carbonyl]-L-leucyl-N-[(1S)-1-formyl-3-methylbutyl]-L-leucinamide (MG 132); N-(6-Chloro-7-methoxy-9H-pyrido[3,4-b]indol-8-yl)-2-methyl-3-pyridinecarboxamide dihydrochloride (ML 120B dihydrochloride); 1-[(4-Methylphenyl)sulfonyl]-1H-benzimidazol-2-amine (ML 130); 8-[[[5-Chloro-2-[3,4-dimethyl-3,4-bis(hydroxymethyl)-1-pyrrolidinyl]-4-pyridinyl]carbonyl]amino]-1-(4-fluorophenyl)-4,5-dihydro-1H-benz[g]indazole-3-carboxamide (PF 184); 4-[(1E)-2-(3,5-Dihydroxyphenyl)ethenyl]-1,2-benzenediol (Piceatannol); PR 39 (porcine) peptide; (9β,13α,14β,20α)-3-Hydroxy-9,13-dimethyl-2-oxo-24,25,26-trinoroleana-1(10),3,5,7-tetraen-29-oic acid methyl ester (Pristimerin); N-(6-Chloro-9H-pyrido[3,4-b]indol-8-yl)-3-pyridinecarboxamide dihydrochloride (PS 1145 dihydrochloride); N-[(Phenylmethoxy)carbonyl]-L-isoleucyl-L-α-glutamyl-tert-butyl ester-N-[(1S)-1-formyl-3-methylbutyl]-L-alaninamide (PSI); Pyrrolidinedithiocarbamate ammonium; 6-(Phenylsulfinyl)tetrazolo[1,5-b]pyridazine (Ro 106-9920); 4-Amino-[2',3'-bithiophene]-5-carboxamide (SC 514); N-[3,5-Bis(trifluoromethyl)phenyl]-2-chloro-4-(trifluoromethyl)-5-pyrimidinecarboxamide (SP 100030); 5-[[4-(2-Pyridylsulfamoyl)phenyl]azo]salicylic acid (Sulfasalazine); 6,7,8,9-Tetrahydro-1,6,6-trimethylphenanthro[1,2-b]furan-10,11-dione (Tanshinone IIA); 2-[(Aminocarbonyl)amino]-5-(4-fluorophenyl)-3-thiophenecarboxamide (TPCA-1), (4β,5β,6β,22R)-5,6-Epoxy-4,22,27-trihydroxy-1-oxoergosta-2,24-dien-26-oic acid 6-lactone (Withaferin A). In some embodiments, the NF-κB signaling pathway inhibitor is Withaferin A.

In some embodiments, the inhibitor is selected from Bithionol, Bortezomib, Cantharidin, Chromomycin A3, Daunorubicinum, Digitoxin, Ectinascidin 743, Emetine, Fluorosalan, Manidipine hydrochloride, Narasin, Lestaurtinib, Ouabain, Sorafenib tosylate, Sunitinib malate, Tioconazole, Tribromsalan, Triclabendazolum, Zafirlukast, and Withaferin A.

In some embodiments, the NF-κB signaling pathway inhibitor is administered parenterally. In some embodiments, the NF-κB signaling pathway inhibitor is administered orally, intraveneously, subcutaneously, or intramuscularly. In some embodiments, the inhibitor is administered by a route described herein. In some embodiments, the inhibitor is administered orally.

The compositions of the present invention may be given in dosages, generally at the maximum amount while avoiding or minimizing any potentially detrimental side effects. The compositions can be administered in effective amounts, alone or in a cocktail with other compounds, for example, other compounds.

In some embodiments, therapeutically effective amounts of compounds of the present invention may range from approximately 0.05 to 500 mg per kilogram body weight of the recipient per day. In some embodiments, the NF-κB signaling pathway inhibitor is administered in a dosage of 0.05, 0.1, 0.5, 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 mg/kg/dose (or any derivable range therein). In some embodiments, the dose is given, once, twice, 3, 4, 5, 6, 7, 8, 9, or 10 times (or any derivable range therein) per day, per week, or per month. In some embodiments, the patient is administered one or more doses on a daily basis or on a weekly basis.

A "subject," "individual" or "patient" is used interchangeably herein and refers to a vertebrate, for example a primate, a mammal or preferably a human. Mammals include, but are not limited to equines, canines, bovines, ovines, murines, rats, simians, humans, farm animals, sport animals and pets. In some embodiments, the subject is a human subject. In some embodiments, the subject has been diagnosed with pancreatitis, acute pancreatitis, chronic pancreatitis, pancreatic cancer, mumps, autoimmune disease, high blood calcium, hypothermia, endoscopic retrograde cholangiopancreatography, pancreas divisum, type 2 diabetes, pancreatic duct stones, vasculitis, coxsakievirus infection, or porphyria.

In some embodiments, the method further comprises administration of pain medication and/or antibiotics. In some embodiments, the method further comprises administration of a traditional therapeutic for pancreatitis, as known in the art and/or described herein.

In some embodiments, the subject is one that is being treated with one or more of corticosteroids, didanosine, pentamidine, diuretics, valproic acid, L-asparaginase, azathioprine, metformin, vidagliptin, and sitagliptin. In some embodiments, the patient is one that is being treated or will be treated with a therapeutic known to cause or be associated with pancreatitis.

Any method may also include treating the patient for pancreatitis, which may include directly administering or providing a therapy. In some embodiments, a practitioner or doctor may prescribe a therapy that the patient administers to herself or himself.

NF-κB signaling pathway inhibitors are known to those of skill in the art. It is defined as a compound or substance that inhibits the activity of NF-κB signaling or proteins of the NF-κB signaling pathway. In some embodiments, the NF-κB signaling pathway inhibitors are inhibitors that have been determined to inhibit the activity of an NF-κB protein. In additional embodiments, the inhibitors are non-naturally occurring compounds or substance, such as chemically synthesized compounds or substance.

Use of the one or more compositions may be employed based on methods described herein. Use of one or more compositions may be employed in the preparation of medicaments for treatments according to the methods described herein. Other embodiments are discussed throughout this application. Any embodiment discussed with respect to one aspect of the invention applies to other aspects of the invention as well and vice versa. The embodiments in the Example section are understood to be embodiments o that are applicable to all aspects of the technology described herein.

As used herein, "treatment" or "therapy" is an approach for obtaining beneficial or desired clinical results. This includes: reduce the alleviation of symptoms, the reduction of pancreatic inflammation, and/or the reduction of pancreatic tissue damage. In some embodiments, the term treatment refers to the inhibition or reduction of inflammation in a subject having pancreatitis.

The term "therapeutically effective amount" refers to an amount of the drug that treats or inhibits pancreatitis in the subject. In some embodiments, the therapeutically effective amount inhibits at least or at most or exactly 100, 99, 98, 96, 94, 92, 90, 85, 80, 75, 70, 65, 60, 55, 50, 40, 30, 20, or 10%, or any derivable range therein, of NF-κB signaling pathway activity.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used in this specification and the claim(s), when referring to a particular therapeutic drug regimen, the words "consisting essentially of" includes therapeutic drug remiments including, as active ingredients, only the recited active ingredients.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Experimental protocol for the development of acute and chronic pancreatitis and treatment with WA. (Ia) Acute pancreatitis was induced by administration of 7 intraperitoneal injections of cerulein (50 ug/kg) at 1 hr interval. (IIa)chronic pancreatitis was induced by administration of 7 intraperitoneal (i.p) injections of cerulein (50 ug/kg) at 1 hr interval, once per week for 4 weeks, sham treated mice were injected with saline, Withaferin treatment group received WA (1.25 mg/kg) one hour before cerulein treatment. (IIb) Stringent chronic pancreatitis was induced by administration of 6 i.p. injections of cerulein (50 ug/kg) at 1 hr interval, twice per week for 8 weeks, WA (0.625 mg/kg) treatment was initiated at week 5, one hour before every cerulein treatment days upto 8 weeks.

FIG. 4. Amylase Chronic Pancreatitis Model. Serum amylase levels increased significantly after administration of cholecystokinin analog cerulein due to acinar damage and leakage of enzyme into the serum. Mice treated with a combination of Cerulein and WA showed significantly lower serum amylase level when compared to cerulein treated mice. Serum was collected at week 3 and week 4 of cerulein treatment, one hour after the last injection. Values are mean±SD (n=6/group)

FIG. 5A-B Cytokine/Chemokine in pancreatic lysate (standard chronic pancreatitis). Luminex analysis of pro-inflammatory cytokine/chemokine in pancreas tissue lysate after standard pancreatitis induction. Pro-inflammatory cytokine (IL-6, 5A) and chemokine (MCP-1, 5B) were elevated in the pancreas of mice treated with cerulein but, WA administration effectively blocked production of both these cytokine and chemokine. Values are mean±SD (n=4/group)

FIG. 6A-B Cytokine/Chemokine in pancreatic lysate (stringent chronic pancreatitis). Luminex analysis of pro-inflammatory cytokine/chemokine in pancreas tissue lysate after induction of stringent pancreatitis. Pro-inflammatory cytokine (IL-6, 5A) and chemokine (MCP-1, 5B) were elevated in the pancreas of mice treated with cerulein but, WA administration effectively blocked production of both these cytokine and chemokine. Values are mean±SD (n=4/group).

FIG. 7A-G. Neutrophil Staining: Immunohistochemical staining of mouse pancreas using granulocyte marker Ly6g. (A, C, E) Nuclear staining using DAPI (Grey foci). (B, D, F) staining with granulocyte marker ly6g (Grey or white foci). (B) control mice pancreas showing very little or no granulocytic infiltration, (D) Cerulein treated mice showing significant infiltration of Ly6g+ inflammatory cells, (F) mice treated with a combination of cerulein and WA showing significantly reduced inflammatory cell infiltration. (G) Semi-quantitative analysis of percentage of Ly6g+ positive cells within the focal point. Values are mean±SD (n=5/group).

FIG. 8A-L. Ki-67 Staining. Immunohistochemical staining of proliferation marker Ki-67 in mouse pancreatic tissue. (A, C, E, G, I, K) Nuclear staining using DAPI (Grey or white foci). (B, D, F, H, J, L) Staining of Ki67+ cells (Grey or white foci). (B, H) very few or no Ki67+ cells are seen in the pancreas of control mice. (D, J) Number of Ki67+ cells are significantly increased in cerulein treated mice, and the severity of CP correlates with number of Ki67+ cells. (F, L) Number of Ki67+ cells are significantly reduced compared to cerulein treated mice. Results are representative of six animals per group.

FIG. 9A-B. Percentage of Ki67+ Cells. Semi-quantitative analysis of percentage of Ki67+ cells present in the pancreas was performed using the ImageJ software. Ki67+ area is significantly increased in mice treated with cerulein. WA administered mice had significantly lower Ki67+ area. (A) Standard CP model, (B) Stringent CP Model. Values are mean±SD (n=5/group).

FIG. 10A-D. NF-κB Staining. Immunohistochemical staining of NF-κB p65 on mouse pancreatic tissue. (A) Control mice pancreas showing P65 (arrows) localization in the cytoplasm, (B) Cerulein treated mice showing significant infiltration of NF-κB P65 protein into the nucleus, (C) WA treatment significantly prevented NF-κB translocation into the nucleus. (D) Protein blot of NF-κB P65 from pancreatic lysate. Cerulein treated mice show overexpression of P65 protein compared to control, WA significantly inhibited overexpression.

FIG. 11A-G. Role of ER stress in CP and inhibition by WA. qRT-PCR analysis of ER stress markers in standard CP model. Cerulein administration leads to significant upregulation of genes responsible for ER stress, but treatment with WA significantly reduced ER stress gene signals. (A) Perk (B) Atf6 (C) Ern1 (D) Eif2a (E) Atf4 (F) xbp1 (G) Chop. Results are shown as mean±SD (n=4/group).

FIG. 12A-G. Role of ER stress in CP and inhibition by WA. qRT-PCR analysis of ER stress markers in stringent CP model. Cerulein administration leads to significant upregulation of genes responsible for ER stress, but treatment with WA significantly reduced ER stress gene signals. (A) Perk (B) Ern1 (C) Atf6 (D) Chop (E) xbp1 (F) eif2a (G) Atf4. Results are shown as mean±SD (n=4/group).

FIG. 13A-E. Inflammasome genes upregulated in CP. qRT-PCR analysis of inflammasome genes in standard CP model. Cerulein administration leads to significant upregulation of genes responsible for inflammasome assembly and activation, but treatment with WA significantly reduced inflammasome related genes. (A) HMGB1 (B) Pycard (C) NLRP3 (D) IL-18 (E) IL-1b. Results are shown as mean±SD (n=4/group).

FIG. 14A-C. Inflammasome genes upregulated in stringent model of CP. qRT-PCR analysis of inflammasome genes in stringent CP model. Cerulein administration leads to significant upregulation of genes responsible for inflammasome assembly and activation, but treatment with WA significantly reduced inflammasome related genes. (A) HMGB1 (B) NLRP3 (C) IL-1b. Results are shown as mean±SD (n=4/group).

FIG. 15A-F. Pro-inflammatory and pro-apoptotic genes upregulated during CP. qRT-PCR analysis of pro-inflammatory and pro-apoptotic genes in standard CP model. Cerulein administration leads to significant upregulation of pro-inflammatory and pro-apoptotic genes regulated mostly by NFκB, but treatment with WA significantly reduced most of these gene signals. (A) IL-6 (B) TNFα (C) Nos2 (D) Casp3 (E) Casp7 (F) Bax. Results are shown as mean±SD (n=4/group).

FIG. 16A-D. Pro-inflammatory and pro-apoptotic genes upregulated during CP. qRT-PCR analysis of pro-inflammatory and pro-apoptotic genes in stringent CP model. Cerulein administration leads to significant upregulation of pro-inflammatory and pro-apoptotic genes regulated mostly by NFκB, but treatment with WA significantly reduced most of these gene signals. (A) IL-6 (B) TNFα (C) Nos2 (D) Bax. Results are shown as mean±SD (n=4/group).

FIG. 18A-I. Inflammatory cell Infiltration. Infiltration of inflammatory cells into the mouse pancreas subjected to acute pancreatitis. Flow cytometric analysis of (A-C)CD45+ CD11b+ myeloid cells (D-F) CD45+Ly6g+ granulocyte cells (G-I) CD45+CD14+ monocytes infiltrating the pancreas after cerulein treatment. (A, D, G) Compared to Control, (B, E, H) cerulein treatment significantly increased percentage of infiltrated innate inflammatory cells, (C, F, I) WA administration demonstrated reduced percentage of infiltrating cells (n=5/group).

FIG. 19A-J. Leucocyte infiltration into pancreas after cerulein injection. Infiltration of leucocytes into the mouse pancreas subjected to acute pancreatitis. Flow cytometric analysis of CD45+ immune cells infiltrating the pancreas after cerulein treatment. (D-F) Cerulein treatment significantly increased percentage of infiltrated CD45+ cells compare to (A-C) control, (G-I) WA administration demonstrated reduced percentage of infiltrating cells, (J) percentage of leucocytes/pancreas is shown (n=5/group).

DETAILED DESCRIPTION OF THE INVENTION

Figure 2:
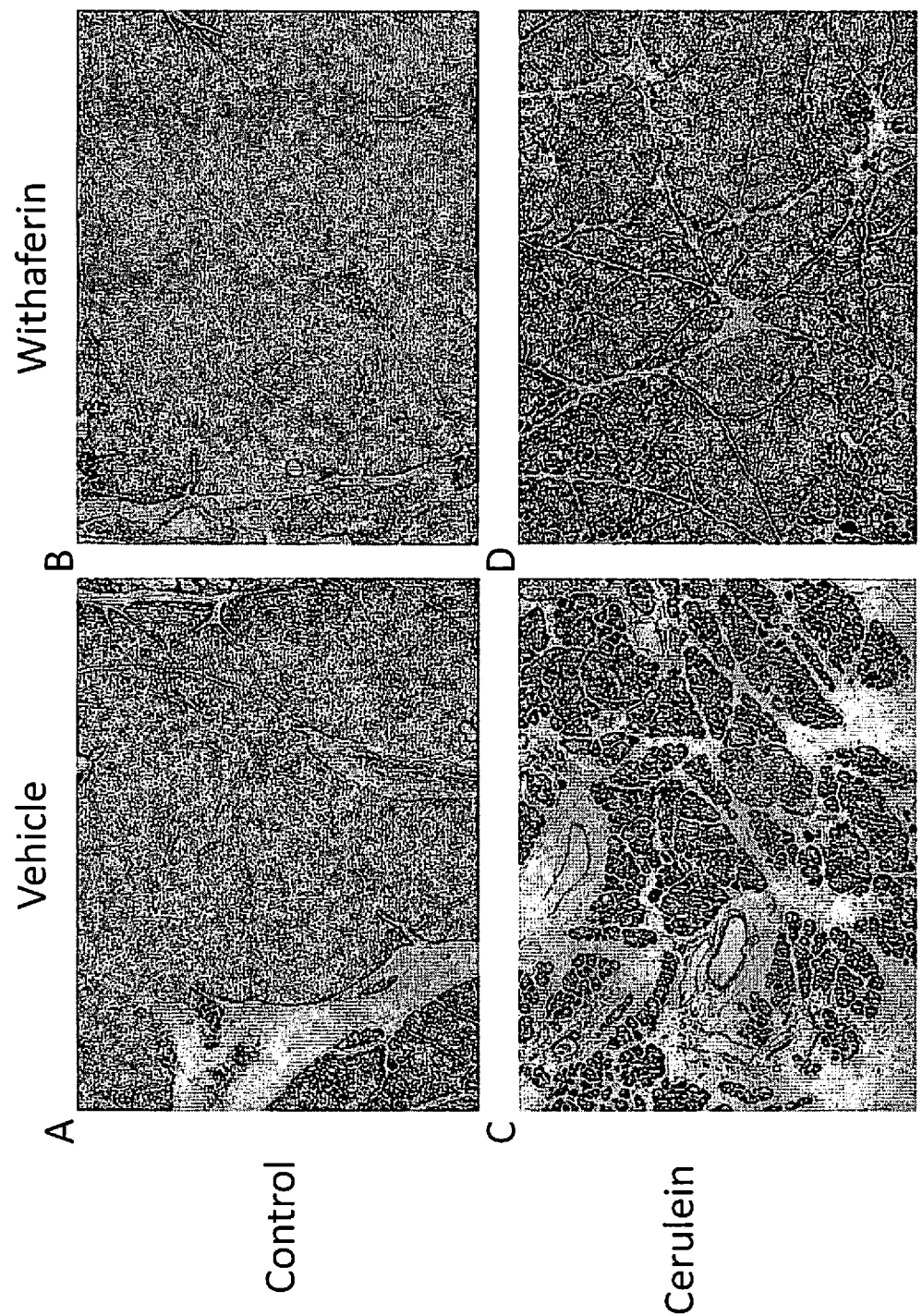
FIG. 2A-D. Histopathology: Chronic Pancreatitis. Histopathological examination of mouse pancreas using hematoxylin and eosin (H&E) staining. (A and B) saline and Withaferin A (WA) (1 mg/kg) treated mouse pancreas respectively showing normal phenotype, (C) Cerulein (50 ug/kg) injected mice demonstrating histomorphological features of severe chronic pancreatitis such as acinar atrophy, inflammatory cell infiltration and ductal metaplasia, (D) mice treated with both WA (1 mg/kg) and cerulein (50 ug/kg) showed significantly reduced severity of chronic pancreatitis based on histopathological assessment. Results are representative of six animals per group.

Inflammatory diseases are often treated with anti-inflammatory medications and/or immunosuppressants. However, there are no standard therapeutic strategies for pharmacologically reducing inflammation in pancreatitis or for treating the disease in any way other than pain management. One reason could be that certain anti-inflammatory drugs are associated with promoting pancreatitis. It was found here that the NF-κB signaling pathway plays a central role in pancreatitis, and inhibition of NF-κB signaling (e.g. by Witherferin A) has the potential to reduce the incidence of pancreatitis and protect pancreatic tissues from inflammatory damage.

I. NF-κB Signaling Pathway and Inhibitors

NF-κB (nuclear factor kappa-light-chain-enhancer of activated B cells) is a protein complex that controls transcription of DNA. NF-κB is found in almost all animal cell types and is involved in cellular responses to stimuli such as stress, cytokines, free radicals, ultraviolet irradiation, oxidized LDL, and bacterial or viral antigens. NF-κB plays a key role in regulating the immune response to infection (K light chains are critical components of immunoglobulins). Incorrect regulation of NF-κB has been linked to various diseases. However, it was not known that NF-κB signaling contributed pancreatitis.

NF-κB family members share structural homology with the retroviral oncoprotein v-Rel, resulting in their classification as NF-κB/Rel proteins. There are five proteins in the mammalian NF-κB family:

| Class | Protein | Aliases | Gene |
|---|---|---|---|
| I | NF-κB1 | p105 → p50 | NF-KB1 |
|   | NF-κB2 | p100 → p52 | NF-KB2 |
| II | RelA | p65 | RELA |
|   | RelB |  | RELB |
|   | c-Rel |  | REL |

NF-κB is important in regulating cellular responses because it belongs to the category of "rapid-acting" primary transcription factors, i.e., transcription factors that are present in cells in an inactive state and do not require new protein synthesis in order to become activated (other members of this family include transcription factors such as c-Jun, STATs, and nuclear hormone receptors). This allows NF-κB to be a first responder to harmful cellular stimuli.

In unstimulated cells, the NF-κB dimers are sequestered in the cytoplasm by a family of inhibitors, called IκBs (Inhibitor of κB), which are proteins that contain multiple copies of a sequence called ankyrin repeats. By virtue of their ankyrin repeat domains, the IκB proteins mask the nuclear localization signals (NLS) of NF-κB proteins and keep them sequestered in an inactive state in the cytoplasm.

IκBs are a family of related proteins that have an N-terminal regulatory domain, followed by six or more ankyrin repeats and a PEST domain near their C terminus. Although the IκB family consists of IκBα, IκBβ, IκBε, and Bcl-3, the best-studied and major IκB protein is IκBα. Due to the presence of ankyrin repeats in their C-terminal halves, p105 and p100 also function as IκB proteins. The c-terminal half of p100, that is often referred to as IκBδ, also functions as an inhibitor. IκBδ degradation in response to developmental stimuli, such as those transduced through LTβR, potentiate NF-κB dimer activation in a NIK dependent non-canonical pathway.

Activation of the NF-κB is initiated by the signal-induced degradation of IκB proteins. This occurs primarily via activation of a kinase called the IκB kinase (IKK). IKK is composed of a heterodimer of the catalytic IKKα and IKKβ subunits and a "master" regulatory protein termed NEMO (NF-κB essential modulator) or IKK gamma. When activated by signals, usually coming from the outside of the cell, the IκB kinase phosphorylates two serine residues located in an IκB regulatory domain. When phosphorylated on these serines (e.g., serines 32 and 36 in human IκBα), the IκB inhibitor molecules are modified by a process called ubiquitination, which then leads them to be degraded by a cell structure called the proteasome.

With the degradation of IκB, the NF-κB complex is then freed to enter the nucleus where it can 'turn on' the expression of specific genes that have DNA-binding sites for NF-κB nearby. The activation of these genes by NF-κB then leads to the given physiological response.

While NF-κB signaling is known to have a role in inflammation, the use of some anti-inflammatory drugs, such as some NSAIDS, has been shown to contribute to pancreatic inflammation. Therefore, it is surprising that administration of an NF-κB signaling such as Withaferin A was able to reduce pancreatitis and protect pancreatic tissues from inflammatory damage in a mouse model for pancreatitis.

In some embodiments, the NF-κB signaling inhibitor is an inhibitor of the activation of the pathway, and can be either upstream or downstream of NF-κB activation. The NF-κB signaling pathway is known in the art and is also described in some detail above. In some embodiments, the NF-κB inhibitor is selected from 2-Amino-6-[2-(cyclopropylmethoxy)-6-hydroxyphenyl]-4-(4-piperidinyl)-3-pyridinecarbonitrile (ACHP); 2-Amino-7-(1-methylethyl)-5-oxo-5H-[1]benzopyrano[2,3-b]pyridine-3-carboxylic acid (Amlexanox); (3E,4S)-3-[2-[(1R,4aS,5R,6R,8aS)-Decahydro-6-hydroxy-5-(hydroxymethyl)-5,8a-dimethyl-2-methylene-1-naphthalenyl]ethylidene]dihydro-4-hydroxy-2(3H)-furanone (Andrographolide); (3R,4R)-4-[(3,4-Dimethoxyphenyl)methyl]dihydro-3-[(4-hydroxy-3-methoxyphenyl)methyl]-2(3H)-furanone (Arctigenin); (2E)-3-[[4-(1,1-Dimethylethyl)phenyl]sulfonyl]-2-propenenitrile (Bay 11-7085); (2E)-3-[(4-Methylphenyl)sulfonyl]-2-propenenitrile (Bay 11-7821); (6E)-6,7,8,9-Tetradeoxy-N-[(3S,6S)-hexahydro-1-methyl-2-oxo-6-[(1-oxotetradecyl)oxy]-1H-azepin-3-yl]-8-methyl-2-O-methyl-D-gulo-Non-6-enonamide (Bengamide B); 3-(3,4-Dihydroxyphenyl)-2-propenoic acid 2-phenylethyl ester (CAPE); 2E)-1-(2,4-Dihydroxy-6-methoxyphenyl)-3-phenyl-2-propen-1-one (Cardamonin); (9β,13α,14β,20α)-3-Hydroxy-9,13-dimethyl-2-oxo-24,25,26-trinoroleana-1(10),3,5,7-tetraen-29-oic acid (Celastrol); 1-[3,5-Bis(1,1-dimethylethyl)-4-hydroxyphenyl]-2-[2-[(3-hydroxypropyl)amino]-5,6-dimethyl-1H-benzimidazol-1-yl]ethanone (CID 2858522); (3R,5aS,6S,10aR)-2,3,5a,6-Tetrahydro-6-hydroxy-3-(hydroxymethyl)-2-methyl-10H-3,10a-epidithiopyrazino[1,2-a]indole-1,4-dione (Gliotoxin); 5,3'-Diallyl-2,4'-dihydroxybiphenyl (Honokiol); (6aS,10aS)-3-(1,1-Dimethylheptyl)-6a,7,10,10a-tetrahydro-1-hydroxy-6,6-dimethyl-6H-dibenzo[b,d]pyran-9-methanol (Dexanabinol); (4Z)-4-(2-Amino-1,5-dihydro-5-oxo-4H-imidazol-4-ylidene)-2-bromo-4,5,6,7-tetrahydropyrrolo[2,3-c]azepin-8(1H)-one (10Z-Hymenialdisine); N-(4-Pyrrolidin-1-yl-piperidin-1-yl)-[4-(4-benzo[b]thiophen-2-yl-pyrimidin-2-ylamino)phenyl]carboxamide hydrochloride (IKK 16); N-[3,5-Bis(trifluoromethyl)phenyl]-5-chloro-2-hydroxybenzamide (IMD 0354); 2-(3,4-Dihydroxyphenyl)-5,7-dihydroxy-4H-1-benzopyran-4-one (Luteolin); N-[(Phenylmethoxy)carbonyl]-L- leucyl-N-[(1S)-1-formyl-3-methylbutyl]-L-leucinamide (MG 132); N-(6-Chloro-7-methoxy-9H-pyrido[3,4-b]indol-8-yl)-2-methyl-3-pyridinecarboxamide dihydrochloride (ML 120B dihydrochloride); 1-[(4-Methylphenyl)sulfonyl]-1H-benzimidazol-2-amine (ML 130); 8-[[[5-Chloro-2-[3,4-dimethyl-3,4-bis(hydroxymethyl)-1-pyrrolidinyl]-4-pyridinyl]carbonyl]amino]-1-(4-fluorophenyl)-4,5-dihydro-1H-benz[g]indazole-3-carboxamide (PF 184); 4-[(1E)-2-(3,5-Dihydroxyphenyl)ethenyl]-1,2-benzenediol (Piceatannol); PR 39 (porcine) peptide; (9β,13α,14β,20α)-3-Hydroxy-9,13-dimethyl-2-oxo-24,25,26-trinoroleana-1(10),3,5,7-tetraen-29-oic acid methyl ester (Pristimerin); N-(6-Chloro-9H-pyrido[3,4-b]indol-8-yl)-3-pyridinecarboxamide dihydrochloride (PS 1145 dihydrochloride); N-[(Phenylmethoxy)carbonyl]-L-isoleucyl-L-α-glutamyl-tert-butyl ester-N-[(1S)-1-formyl-3-methylbutyl]-L-alaninamide (PSI); Pyrrolidinedithiocarbamate ammonium; 6-(Phenylsulfinyl)tetrazolo[1,5-b]pyridazine (Ro 106-9920); 4-Amino-[2',3'-bithiophene]-5-carboxamide (SC 514); N-[3,5-Bis(trifluoromethyl)phenyl]-2-chloro-4-(trifluoromethyl)-5-pyrimidinecarboxamide (SP 100030); 5-[[4-(2-Pyridylsulfamoyl)phenyl]azo]salicylic acid (Sulfasalazine); 6,7,8,9-Tetrahydro-1,6,6-trimethylphenanthro[1,2-b]furan-10,11-dione (Tanshinone IIA); 2-[(Aminocarbonyl)amino]-5-(4-fluorophenyl)-3-thiophenecarboxamide (TPCA-1); (4β,5β,6β,22R)-5,6-Epoxy-4,22,27-trihydroxy-1-oxoergosta-2,24-dien-26-oic acid 6-lactone (Withaferin A). Alternatively, the inhibitor is one known in the art to be a NF-κB inhibitor.

In some embodiments, the inhibitor is selected from Bithionol, Bortezomib, Cantharidin, Chromomycin A3, Daunorubicinum, Digitoxin, Ectinascidin 743, Emetine, Fluorosalan, Manidipine hydrochloride, Narasin, Lestaurtinib, Ouabain, Sorafenib tosylate, Sunitinib malate, Tioconazole, Tribromsalan, Triclabendazolum, Zafirlukast, and Withaferin A.

II. Therapeutic Methods

The methods described herein may be used to treat or prevent pancreatitis in a patient in need thereof. In some embodiments, the patient is one that has been diagnosed with pancreatitis, acute pancreatitis, chronic pancreatitis, pancreatic cancer, mumps, autoimmune disease, high blood calcium, hypothermia, endoscopic retrograde cholangiopancreatography, pancreas divisum, type 2 diabetes, pancreatic duct stones, vasculitis, coxsakievirus infection, or porphyri. In some embodiments, the patient is one that has been diagnosed with pancreatitis. In some embodiments, the patient does not have and/or has not been diagnosed with pancreatic cancer. In some embodiments, the patient is not one who is being treated for pancreatic cancer.

In some embodiments, the patient is one that is at risk of developing pancreatitis such as one that is taking a drug known to be associated with pancreatitis. In some embodiments, the patient is one that is being treated with one or more of corticosteroids, didanosine, pentamidine, diuretics, valproic acid, L-asparaginase, azathioprine, metformin, vidagliptin, and sitagliptin. The treatment may be before the NF-κB signaling pathway inhibitor or after administration of the NF-κB signaling pathway inhibitor.

III. Pharmaceutical Compositions

Embodiments include methods for pancreatits. Administration of the compositions will typically be via any common route. This includes, but is not limited to oral, parenteral, orthotopic, intradermal, subcutaneous, intramuscular, intraperitoneal, intranasal, or intravenous injection. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%. In some embodiments, the compositions are administered orally.

Typically, compositions are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner.

The manner of application may be varied widely. Any of the conventional methods for administration of an antibody are applicable. These are believed to include oral application on a solid physiologically acceptable base or in a physiologically acceptable dispersion, parenterally, by injection and the like. The dosage of the pharmaceutical composition will depend on the route of administration and will vary according to the size and health of the subject.

In many instances, it will be desirable to have multiple administrations of at most about or at least about 3, 4, 5, 6, 7, 8, 9, 10 or more. The administrations may range from 2 day to twelve week intervals, more usually from one to two week intervals. The course of the administrations may be followed by assays for NF-κB activity.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated.

The NF-κB signaling pathway inhibitors can be formulated for parenteral administration, e.g., formulated for injection via the intravenous, intradermal, intramuscular, sub-cutaneous, or even intraperitoneal routes. In some embodiments, the composition is administered by intravenous injection. The preparation of an aqueous composition that contains an active ingredient will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredients in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

IV. Combination Therapy

The compositions and related methods, particularly administration of a NF-κB signaling pathway inhibitor may also be used in combination with the administration of traditional therapies. Traditional therapies for chronic pancreatitis focus on control of pain, improvement of maldigestion, and management of complications.

Treatment options for pain relief from chronic pancreatitis include abstinence from alcohol and smoking, analgesics, and pancreatic enzymes. Pancreatic enzymes are presumed to improve pain by suppressing CCK release from the duodenum, leading to decreased pancreatic stimulation. Interestingly, many patients with chronic pancreatitis have nonvisceral pain (central or somatosensory in origin). A differential nerve blockade is helpful in determining whether there is a central or somatosensory component to the pain syndrome. A differential nerve blockade is indicated for any patient with pancreatic pain that does not respond to simple medical therapeutic measures such as non-narcotic analgesics and enzymes. Antidepressants, anticonvulsants (gabapentin), topical therapy, psychiatric counseling, and opioid rehabilitation may be of use for patients with nonvisceral pain. Celiac or sphlanchnic nerve blockade may be used in select patients with visceral pancreatic pain. Limited studies have suggested that a subset of patients obtain significant short-term pain relief from CT-guided celiac plexus blockade. EUS-guided celiac plexus blockade has emerged as an effective and perhaps safer alternative to percutaneous methods. It is generally accepted that pain in chronic pancreatitis can result in part from obstruction of the main pancreatic duct from stones and strictures, leading to increased ductal and parenchymal pressure. Because obstruction contributes to pain, patients with an enlarged, obstructed main pancreatic duct might benefit from endoscopic therapy, lithotripsy or surgical duct decompression therapy. Endoscopic techniques include biliary or pancreatic sphincterotomy (or both), removal of pancreatic duct stones, and placement of pancreatic stents. Extracorporeal shockwave lithotripsty (ESWL) is also an effective ancillary treatment for patients with pancreaticductal stones either alone or in combination of endoscopic therapy. In experienced centers ESWL alone is equally effective compared to combined ESWL and endoscopic therapy, and maybe more cost effective.

Several surgical options exist for select patients with visceral pain resulting from chronic pancreatitis. In patients with a dilated main pancreatic duct, a side-to-side pancreaticojejunostomy (Puestow procedure) may be performed. Pancreatic resection is reserved for patients with disease of the small duct and pain unresponsive to medical therapy. The Whipple procedure and distal pancreatectomy have been used in the past to treat patients with small-duct chronic pancreatitis. Pancreatic enzymes are used for the treatment of maldigestion in chronic pancreatitis. Exogenous pancreatic enzymes are safe, are well tolerated, and produce few side effects. Pancreatic enzyme preparations differ based on enzyme content, the use of microspheres versus microtablets, and the presence of a coating for delayed release. Lipase is the most important determinant of the effectiveness of individual preparations. A minimum of 30,000 U lipase per meal allows adequate intraluminal digestion of fat and protein in most patients.

Acute pancreatitis is traditionally treated with pain medications, IV fluids, and/or fasting. In some cases, therapy is needed to drain fluid that has collected in or around the pancreas, remove gallstones, remove blockages of the pancreatic duct, and, in the most severe cases, surgery is needed to remove damaged, dead or infected pancreatic tissue.

Response to enzyme therapy may be monitored through an assessment of symptoms or, more objectively, through 72-hour stool fat quantification. A poor response to pancreatic enzymes can suggest noncompliance, loss of enzyme potency, improper timing of enzymes in relation to meals, or coexisting mucosal disease. A daily proton pump inhibitor may be added for those refractory to therapy because gastric acid can denature exogenous enzymes.

NF-κB signaling pathway inhibitor treatment may precede or follow the other treatment by intervals ranging from minutes to weeks. In embodiments where the other agents are administered separately, one would generally ensure that a significant period of time did not expire between the time of each delivery, such that the agent and antibody would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Administration of pharmaceutical compositions to a patient/subject will follow general protocols for the administration of such compounds, taking into account the toxicity, if any. It is expected that the treatment cycles would be repeated as necessary.

Various combinations with the NF-κB inhibitor and a traditional therapy may be employed, for example, an NF-κB inhibitor is "A" and the traditional therapy (or a combination of such therapies) given as part of a treatment for pancreatitis, is "B":

| A/B/A | B/A/B | B/B/A | A/A/B | A/B/B | B/A/A |
|---|---|---|---|---|---|
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of pharmaceutical compositions to a patient/subject will follow general protocols for the administration of such compounds, taking into account the toxicity, if any. It is expected that the treatment cycles would be repeated as necessary.

Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of particular embodiments, are exemplary, and are not intended as limitations on the scope of the invention. Changes therein and other uses which are encompassed within the spirit of the invention as defined by the scope of the claims will occur to those skilled in the art.

Example 1: Treatment of Pancreatits with Withaferin A in a Mouse Model for Chronic Pancreatitis Chronic pancreatitis (CP) is a progressive inflammatory disease that results in irreversible loss of pancreatic acinar cells and subsequently the islet cells. The causes of pancreatitis may be genetic mutation, alcohol consumption, pancreatic trauma, autoimmunity, recurrent acute pancreatitis and in many cases idiopathic. Cerulein administration to mice is a well-established model for investigating chronic pancreatitis. Withaferin A (WA) is a steroidal lactone derived from the plant Withania somnifera. WA is a strong blocker of NF-κB signaling pathway and has been shown to protect islets from inflammatory cytokine mediated damage. In this Example, Applicants tested WA for protection of acinar cells from damage caused by cerulein-induced pancreatitis.

C57BL/6 mice were injected with 7 hourly IP injections of cerulein at 50 g/kg once per week for 4 weeks in a standard model for chronic pancreatitis or 6 hourly IP injections of cerulein at 50 g/kg twice per week for 8 weeks in a stringent model for chronic pancreatitis. WA was administered one hour prior to cerulein beginning in week 1 in the standard model and beginning in week 5 in the stringent model of chronic pancreatits. Incidence of pancreatitis was confirmed by histopathological analysis of pancreas tissue, serum amylase levels, and neutrophil infiltration into pancreatic tissue. Cell proliferation was assessed by Ki67 staining. Pancreatic stone protein REG1α was analyzed by immunohistochemical staining. ImageJ software was used to quantify the area of positively stained cells.

Figure 3:
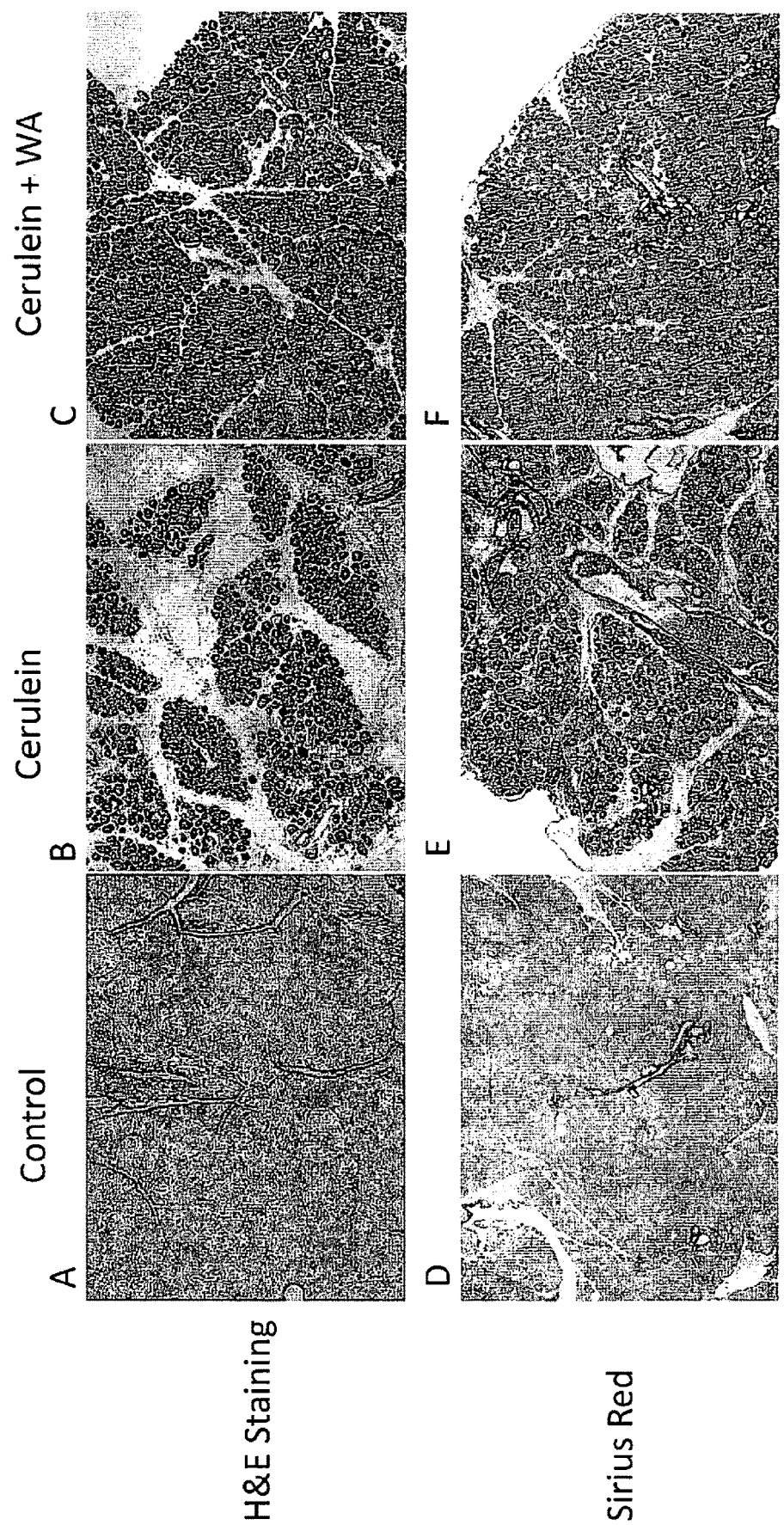
FIG. 3A-F. Histopathology: Stringent Chronic Pancreatitis. Histopathological examination of mice pancreas subjected to a stringent model of pancreatitis. (A-C) H&E staining of mouse pancreas, (D-F) Sirius red staining to visualize fibrotic change of pancreatic parenchyma. (A and D) Saline treated mice showed normal pancreas histology and no fibrosis, (B and E) Cerulein (50 ug/kg) injected mice showed morphological features of severe chronic pancreatitis and pancreatic tissue has been replaced with fibrotic tissue, (C and F) Cerulein (50 ug/kg) and Withaferin (0.5 mg/kg) treated mice showed significantly reduced pancreas damage and fibrosis. Results are representative of six animals per group.

Histopathological analysis of the pancreatic tissue revealed acinar cell atrophy and mononuclear cell infiltration in the cerulein injected mice in the standard (FIG. 2C) and stringent (FIGS. 3B and 3E), whereas, WA treatment significantly reduced acinar cell atrophy and infiltration of mononuclear cells (FIGS. 2D, 3C, and 3F). Serum amylase levels were elevated in the cerulein treated mice compared to the control mice, and this was significantly decreased by WA (952.8±228.8 versus 696.3±98.6 nmol/min/mL; p=0.045) (FIG. 4). Large number of neutrophils migrated into pancreas of cerulein treated mice (FIGS. 7D and 7G), whereas in WA treated mice pancreas there was little to no infiltration of neutrophils (3,742±1,188 versus 719±276 cells per objective field at a magnification of ×200; p=0.03) (FIGS. 7F and 7G). Mice treated with WA and cerulein had very low number of Ki67+ cells in the pancreas (FIGS. 8F and 8I; See also FIG. 9A-B) compared to cerulein only treated mice (FIGS. 8D and 8J; See also FIG. 9A-B) (cerulein versus WA+cerulein; 20.0±16.0 versus 3.8±2.9). Immunohistochemical staining revealed that REG1α was upregulated in cerulein treated mice pancreas, but WA treatment brought REG1α to control levels (3,779±448 versus 544±43; p=0.003). NF-κB (FIG. 10A-C) and P65 (FIG. 10D) was also increased in Cerulein-treated mice (FIG. 10B) compared to cerulean and WA treatment (FIG. 10C). Furthermore, genes involved in ER stress (FIG. 11 and FIG. 12), inflammasone (FIG. 13 and FIG. 14), and inflammation and apoptosis (FIGS. 15 and 16) were increased in cerulein-treated mice, but decreased in cerulein and WA treated mice.

In conclusion, NF-κB signaling pathway plays a central role in cerulein-induced pancreatitis. WA, a strong inhibitor of NF-κB, has the potential to reduce the incidence of pancreatitis and protect acinar cells from inflammatory damage.

Materials and Methods:

Mice: All mice were housed in filter topped shoebox cages with autoclaved food and water. C57BL/6 mice purchased from Jackson Laboratories were used throughout the study and all experiments were conducted on age and sex matched littermates. Mice were randomly assigned to control and experimental groups. All experiments were performed in accordance to Baylor Research Institute IACUC guidelines and regulations.

Reagents: Cerulein was purchased from Sigma Aldrich (St. Louis, Mo.), Withaferin A (WA) from Enzo life sciences (Farmingdale, N.Y.). Amylase activity kit, picro Sirius red staining kit, anti-neutrophil and anti-Ki-67 antibody was obtained from Abcam (Cambridge, Mass.). Mouse CD45 antibody was purchased from Biolegend (San Diego, Calif.). Anti-NFκB antibody was bought from Santa-cruz biotechnology (Dallas, Tex.). RNAlater and TRIzol were purchased from Life Technologies (Carlsbad, Calif.). High capacity cDNA reverse transcription kit was obtained from Applied Biosystems (Waltham, Mass.) and qRT-PCR SYBR green/ROX master mix from Qiagen (Valencia, Calif.).

Acute pancreatitis (AP) model: Animals were fasted overnight prior to induction of pancreatitis by cerulein, water was given ad-libitum. Mice were injected with Cerulein (50 ug/kg intraperitoneally) or saline every hour for a total of 7 injections and were sacrificed 1 hr after the last injection. WA (1.25 mg/kg) was administered 1 hr before first cerulein injection (n=5 mice/group). Blood was collected from the inferior vena cava for analysis of serum markers of pancreatitis and pancreas tissue was harvested immediately after sacrifice. Pancreas was divided for immunohistochemistry, RNA extraction, protein extraction, immune cell infiltration analysis.

Chronic pancreatitis (CP) model: Animals were subjected to repeated episodes of acute pancreatitis by supramaximal dose (50 ug/kg) of cerulein administration. Standard Chronic pancreatitis: Mice were fasted overnight prior cerulein injection with ad-libitum supply of water. CP was induced when cerulein was injected i.p. (50 ug/kg) every hour for a total of 7 injection, this injection was repeated once a week for 4 weeks. Control mice were injected with saline as sham treatment. Another group of mice received WA (1.25 mg/kg) 1 hr before the first cerulein injection every week (n=6 mice/group). Mice were then sacrificed and blood and tissue were processed as previously mentioned. Stringent chronic pancreatitis: Mice were fasted overnight prior cerulein injection with ad-libitum supply of water. CP was induced when cerulein was injected i.p. (50 ug/kg) every hour for a total of 6 injection, this injection was repeated twice a week for 8 weeks. WA (0.625 mg/kg) was injected 1 hr prior to first cerulein injection but administration was initiated at week 5 and continued till the end of the experiment. Mice were then sacrificed and tissue was harvested as previously mentioned.

Amylase activity assay: Serum samples obtained from mice after treatment were aliquoted and stored at −80 C until further analysis. Serum was analyzed for amylase activity as per the manufacturer's protocol.

Histology and Immunohistochemistry: Pancreas tissue was placed in 10% formalin immediately after harvesting and fixed for at least 48 hrs at 4° C. before processing. Tissue samples were paraffin embedded and 5 um sections were made and mounted on slides for staining. Hematoxylin and Eosin (H&E) staining was performed for histopathological evaluation. Sirius Red Staining was performed as per manufacturer's protocol on the sections to evaluate fibrotic change in the tissue section. To perform immunohistochemical staining, the sections were deparaffinized in xylene and rehydrated using ethanol. The slides were incubated in a citrate buffer of pH 6 with at 97° C. for 20 minutes. Following the antigen retrieval process, the slides were carefully washed 3 times for 5 minutes in Tris-buffered saline (TBS) containing 0.025% Triton X-100. The slides were blocked in 1% bovine serum albumin (BSA) in TBS for 2 hours at room temperature to block non-specific binding of the antibodies. Then the slides were incubated overnight with primary antibodies which were diluted in TBS with 1% BSA. The following day, the slides were gently rinsed 3 times for 5 minutes in TBS 0.025% Triton X-100. TRITC or FITC labelled secondary antibodies from Invitrogen were diluted in TBS with 1% BSA. The slides were counterstained with DAPI and mounted for microscopic analysis. ImageJ software was used to perform semi-quantitative analysis of the staining.

Immune cell infiltration assay: Cell suspension was prepared from the pancreas tissue after digestion with collagenase (2 mg/mL) at 37° C. for 15 mins. Tissue was further mechanically digested by pipetting several times, the suspension was then washed and filtered to obtain only the single cell fraction. Cell suspension obtained was used for flow cytometric analysis of infiltrated immune cells. $1 \times 10^6$ pancreatic cells were labelled with anti-CD45, anti-CD11b, anti-CD14, and anti-Ly6g antibodies. Stained cells were detected using FACScanto II and data were analyzed using FlowJo software.

qRT-PCR: Pancreas tissue samples were stored in RNAlater at −80° C. until extraction procedure. Total RNA from the pancreas tissue were extracted using TRIzol reagent. Tissue was homogenized and debris was removed by centrifugation. Chloroform was added to separate the RNA from other biomolecules, and further precipitated using iso-propanol. RNA pellet was washed with ethanol and quantified using nanodrop 2000. cDNA synthesis was performed using high capacity cDNA reverse transcription kit as per manufacturer's protocol. PCR primers for 18s rRNA, Perk, Atf6, Ern1, Eif2a, Atf4, Xbp1, Chop, Hmgb1, Pycard, Nlrp3, Il18, Il1b, Il6, Tnfα, Nos2, Casp3, Casp7, Bax were purchased from Qiagen. qRT-PCR was performed using qRT-PCR SYBR green/ROX master mix from Qiagen as per manufacturer's protocol.

Figure 17:
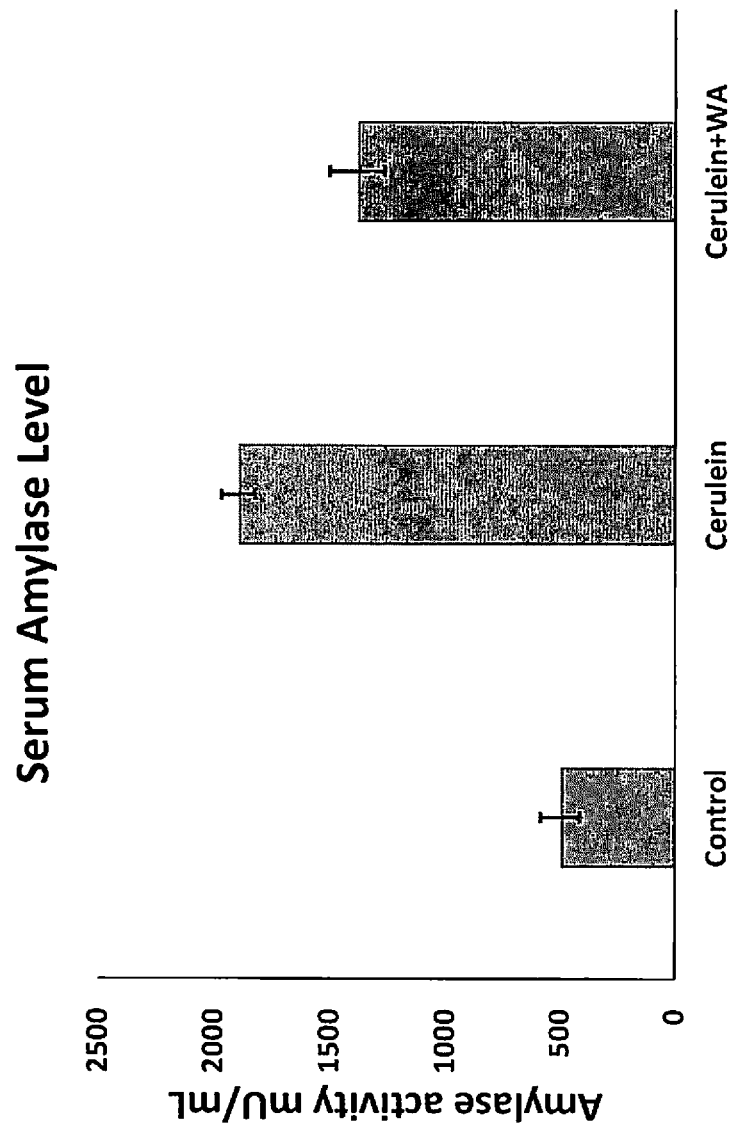
FIG. 17. Serum amylase level in acute pancreatitis model. Serum amylase increased in mice subjected to cerulein induced acute pancreatitis. WA treated group showed significantly reduced serum amylase compared to cerulein treated mice. Serum samples were collected one hour after last cerulein injection on week 1. values are mean±SD (n=5/group).
Figure 19J:
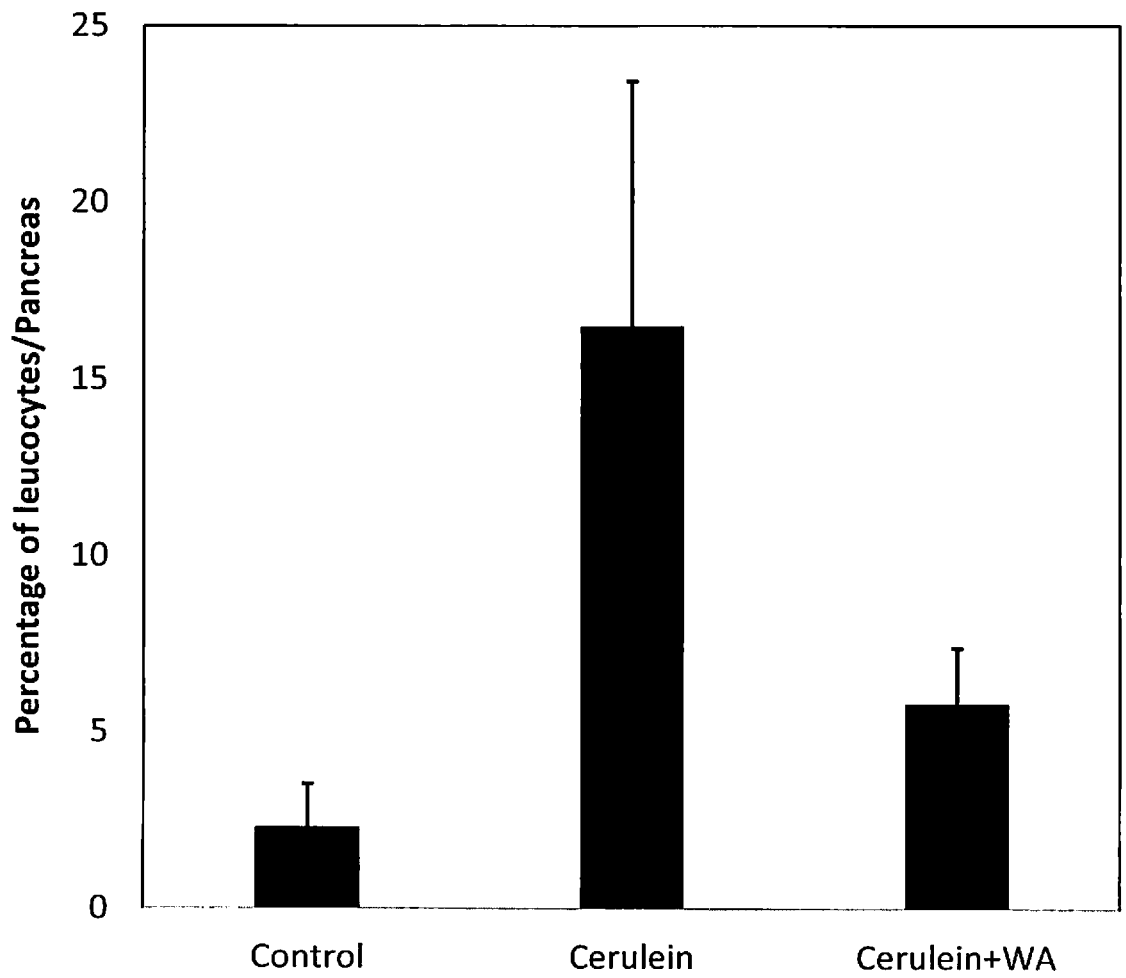
Figure 20:
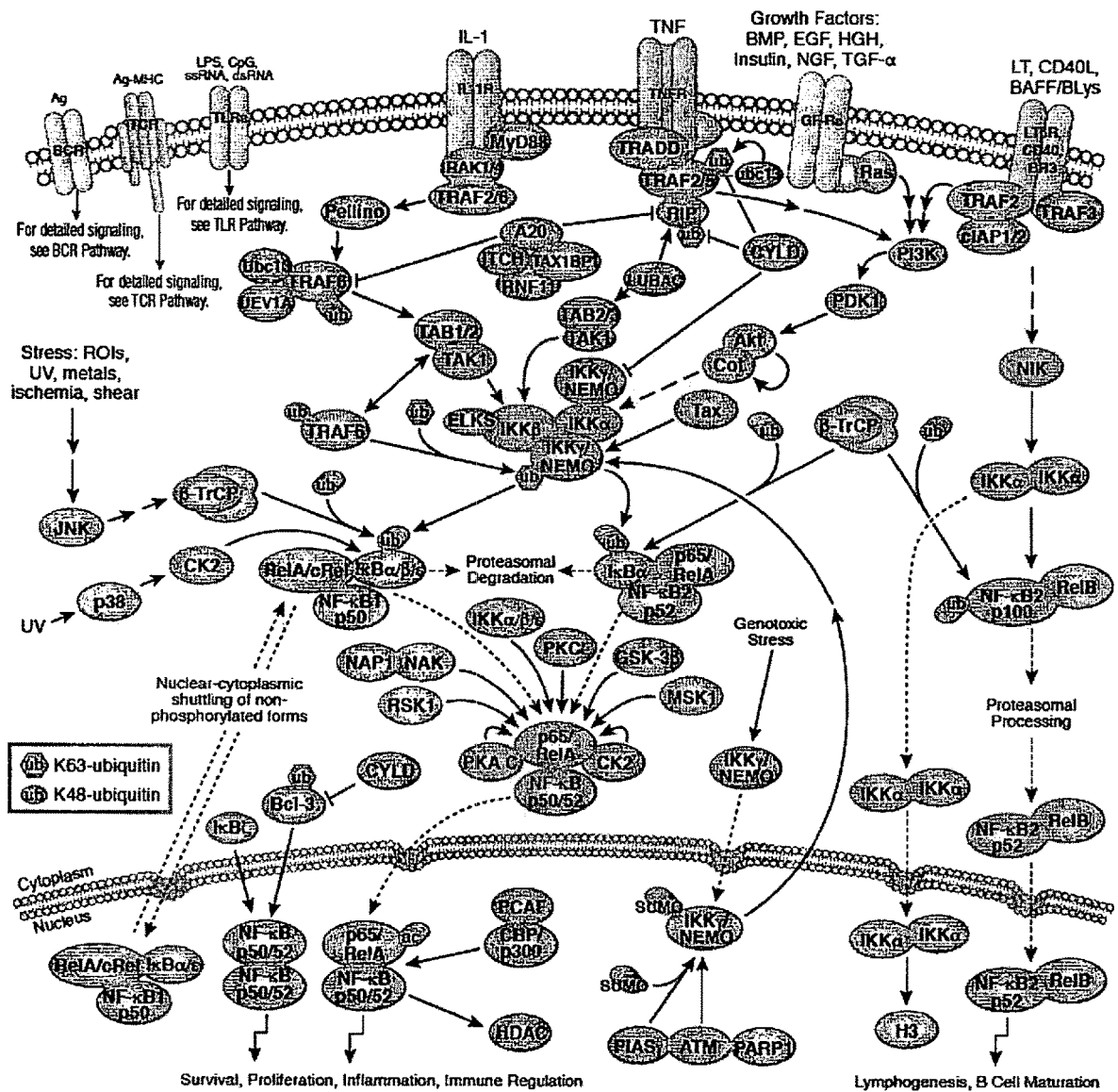
FIG. 20 NF-κB Signaling Pathway and components. Shown is a detailed depiction of the NF-κB Signaling Pathway and proteins that act as activators or inhibitors of the pathway. Pointed arrows indicate an activation of the pathway, and blunted lines (⊥) indicate an inhibitor of the pathway.

Example 2: Treatment of Pancreatits with Withaferin A in a Mouse Model for Acute Pancreatitis To model acute pancreatitis, C57BL/6 mice were injected with 7 hourly IP injections of cerulein at 50 µg/kg. WA (1.25 mg/kg) was administered one hour prior to cerulein. Serum amylase levels were elevated in the cerulein treated mice compared to the control mice, and this was significantly decreased by WA (FIG. 17). Inflammatory cell infiltration was increased in cerulein-treated mice (FIGS. 18B, 18E, and 18H) compared to controls (FIGS. 18A, 18D, and 18G), but were reduced in cerulein and WA-treated mice (FIGS. 18C, 18F, and 18I) compared to cerulein-treated mice. Leucocyte cell infiltration was also increased in cerulein-treated mice (FIGS. 19D, 19E, and 19F) compared to controls (FIGS. 19A, 19B, and 19C), but were reduced in cerulein and WA-treated mice (FIGS. 19G, 19H, and 19I) compared to cerulein-treated mice.

The invention claimed is:

1. A method for inhibiting or treating pancreatitis by inhibiting pancreatic cell atrophy in a subject having pancreatitis, the method comprising administering a therapeutically effective amount of Withaferin A to the subject.

2. The method of claim 1, wherein the subject has been diagnosed with acute or chronic pancreatitis.

3. The method of claim 2, wherein the subject has been diagnosed with chronic pancreatitis.

4. The method of claim 3, wherein the method is for treating chronic pancreatitis by inhibiting the progression of chronic pancreatitis in the subject.

5. The method of claim 1, wherein the subject is determined to not have pancreatic cancer or has not been diagnosed with pancreatic cancer.

6. The method of claim 1, wherein the Withaferin A is administered orally, intravenously, subcutaneously, or intramuscularly.

7. The method of claim 6, wherein the Withaferin A is administered orally.

8. The method of claim 1, wherein the method further comprises administration of pain medication and/or antibiotics.

9. The method of claim 1, wherein the subject is one that is being treated with one or more of corticosteroids, didanosine, pentamidine, diuretics, valproic acid, L-asparaginase, azathioprine, metformin, vidagliptin, and sitagliptin.

* * * * *